United States Patent
Beduneau et al.

(10) Patent No.: US 9,364,443 B2
(45) Date of Patent: Jun. 14, 2016

(54) COMPOSITIONS AND METHODS FOR DRUG DELIVERY

(75) Inventors: Arnaud Beduneau, Lincoln, NE (US); Howard Gendelman, Omaha, NE (US); Barrett Rabinow, Skokie, IL (US); Jane Werling, Arlington Heights, IL (US)

(73) Assignees: BAXTER INTERNATIONAL, INC., Deerfield, IL (US); BAXTER HEALTHCARE SA, Glattpark (Opfikon) (CH); BOARD OF REGENTS OF THE UNIVERSITY OF NEBRASKA, Lincoln, NE (US)

( * ) Notice: Subject to any disclaimer, the term of this patent is extended or adjusted under 35 U.S.C. 154(b) by 917 days.

(21) Appl. No.: 12/398,894

(22) Filed: Mar. 5, 2009

(65) Prior Publication Data
US 2009/0274765 A1 Nov. 5, 2009

Related U.S. Application Data

(60) Provisional application No. 61/068,151, filed on Mar. 5, 2008, provisional application No. 61/205,259, filed on Jan. 20, 2009, provisional application No. 61/148,917, filed on Jan. 30, 2009.

(51) Int. Cl.
| | | |
|---|---|---|
| A61K 31/337 | (2006.01) | |
| A61K 9/51 | (2006.01) | |
| A61K 9/14 | (2006.01) | |
| A61K 47/48 | (2006.01) | |
| C07K 16/28 | (2006.01) | |

(52) U.S. Cl.
CPC .............. *A61K 9/5115* (2013.01); *A61K 9/146* (2013.01); *A61K 9/5161* (2013.01); *A61K 9/5169* (2013.01); *A61K 31/337* (2013.01); *A61K 47/48561* (2013.01); *A61K 47/48853* (2013.01); *A61K 47/48861* (2013.01); *C07K 16/283* (2013.01); *Y10T 428/2991* (2015.01)

(58) Field of Classification Search
CPC ... A61K 9/5115; A61K 9/146; A61K 9/5161; A61K 9/5169; A61K 31/337; A61K 47/45861; A61K 47/48853; C07K 16/283
See application file for complete search history.

(56) References Cited

U.S. PATENT DOCUMENTS

| | | | |
|---|---|---|---|
| 4,224,313 A | 9/1980 | Zimmermann et al. | |
| 4,269,826 A | 5/1981 | Zimmermann et al. | |
| 4,289,756 A | 9/1981 | Zimmermann et al. | |
| 4,608,278 A | 8/1986 | Frank et al. | |
| 4,670,185 A | 6/1987 | Fujiwara et al. | |
| 4,826,689 A | 5/1989 | Violanto | |
| 4,973,465 A | 11/1990 | Baurain et al. | |
| 4,997,454 A | 3/1991 | Violante et al. | |
| 5,091,188 A | 2/1992 | Haynes | |
| 5,100,591 A | 3/1992 | Leclef et al. | |
| 5,118,528 A | 6/1992 | Fessi et al. | |
| 5,145,684 A | 9/1992 | Liversidge et al. | |
| 5,188,837 A | 2/1993 | Domb | |
| 5,216,130 A * | 6/1993 | Line et al. | 530/362 |
| 5,560,932 A | 10/1996 | Bagchi et al. | |
| 5,662,883 A | 9/1997 | Bagchi et al. | |
| 5,665,331 A | 9/1997 | Bagchi et al. | |
| 5,716,642 A | 2/1998 | Bagchi et al. | |
| 5,720,551 A | 2/1998 | Shechter | |
| 5,780,062 A | 7/1998 | Frank et al. | |
| 5,981,719 A | 11/1999 | Woiszwillo et al. | |
| 6,090,925 A | 7/2000 | Woiszwillo et al. | |
| 6,143,211 A | 11/2000 | Mathiowitz et al. | |
| 6,235,224 B1 | 5/2001 | Mathiowitz et al. | |
| 6,268,053 B1 | 7/2001 | Woiszwillo et al. | |
| 6,331,299 B1 | 12/2001 | Rothman et al. | |
| 6,455,073 B1 | 9/2002 | Meredith et al. | |
| 6,458,387 B1 | 10/2002 | Scott et al. | |
| 6,607,784 B2 | 8/2003 | Kipp et al. | |
| 6,616,869 B2 | 9/2003 | Mathiowitz et al. | |
| 6,632,671 B2 | 10/2003 | Unger | |
| 6,638,621 B2 * | 10/2003 | Anderson | 428/402.24 |
| 6,645,464 B1 | 11/2003 | Hainfeld | |
| 6,790,455 B2 | 9/2004 | Chu et al. | |
| 6,835,396 B2 | 12/2004 | Brynjelsen et al. | |
| 6,869,617 B2 | 3/2005 | Kipp et al. | |
| 6,884,436 B2 | 4/2005 | Kipp et al. | |
| 6,902,743 B1 | 6/2005 | Setterstrom et al. | |
| 7,037,528 B2 | 5/2006 | Kipp et al. | |
| 2001/0042932 A1 | 11/2001 | Mathiowitz et al. | |
| 2002/0127278 A1 | 9/2002 | Kipp et al. | |
| 2002/0164694 A1 | 11/2002 | Moore et al. | |
| 2002/0168402 A1 | 11/2002 | Kipp et al. | |
| 2002/0176935 A1 | 11/2002 | Kipp et al. | |
| 2003/0022846 A1 | 1/2003 | Meredith et al. | |
| 2003/0054035 A1 | 3/2003 | Chu et al. | |
| 2003/0059472 A1 | 3/2003 | Brynjelsen et al. | |
| 2003/0092069 A1 | 5/2003 | Kuroda et al. | |

(Continued)

FOREIGN PATENT DOCUMENTS

| | | |
|---|---|---|
| EP | 1952825 | 8/2008 |
| JP | 60-150826 | 8/1985 |

(Continued)

OTHER PUBLICATIONS

Thiele et al., (Biomaterials. 2003. 24;1409-1418).*

(Continued)

*Primary Examiner* — Cherie M Stanfield
(74) *Attorney, Agent, or Firm* — Marshall, Gerstein & Borun LLP

(57) ABSTRACT

The present disclosure is directed to surface-modified particles and to methods of making and using the same. The surface-modified particles comprise a particle core and a coating associated with the particle core, wherein the particle core comprises an active agent, the coating comprises an opsonin, and the surface-modified particle has an average size from about 1 nm to about 2,000 nm.

23 Claims, 7 Drawing Sheets

(56) References Cited

U.S. PATENT DOCUMENTS

| | | | |
|---|---|---|---|
| 2003/0206959 | A9 | 11/2003 | Kipp et al. |
| 2003/0211083 | A1 | 11/2003 | Vogel et al. |
| 2004/0022861 | A1 | 2/2004 | Williams et al. |
| 2004/0043077 | A1 | 3/2004 | Brown |
| 2004/0062756 | A1 | 4/2004 | Humeau et al. |
| 2005/0037083 | A1 | 2/2005 | Brynjelsen et al. |
| 2005/0084456 | A1 | 4/2005 | Tang et al. |
| 2005/0112141 | A1 | 5/2005 | Terman |
| 2005/0176933 | A1 | 8/2005 | Chen et al. |
| 2005/0244503 | A1 | 11/2005 | Rabinow et al. |
| 2006/0073199 | A1 | 4/2006 | Chaubal et al. |
| 2009/0047337 | A1 | 2/2009 | Mescheder et al. |
| 2010/0226970 | A1 | 9/2010 | McDonald et al. |

FOREIGN PATENT DOCUMENTS

| | | | |
|---|---|---|---|
| JP | 2003/514768 | A | 4/2003 |
| JP | 2008/540364 | A | 11/2008 |
| WO | WO-92/11846 | | 7/1992 |
| WO | WO-92/17214 | | 10/1992 |
| WO | WO-94/07999 | | 4/1994 |
| WO | WO-97/14407 | | 4/1997 |
| WO | WO-98/01162 | | 1/1998 |
| WO | WO-98/47492 | | 10/1998 |
| WO | WO-99/00113 | | 1/1999 |
| WO | WO-99/13054 | | 3/1999 |
| WO | WO-00/64954 | | 11/2000 |
| WO | WO-01/58431 | | 8/2001 |
| WO | WO 01/82899 | A2 | 11/2001 |
| WO | WO-02/055059 | | 7/2002 |
| WO | WO-02/060416 | | 8/2002 |
| WO | WO-02/082074 | | 10/2002 |
| WO | WO-2004/035768 | | 4/2004 |
| WO | WO-2004/110270 | | 12/2004 |
| WO | WO-2004/112747 | | 12/2004 |
| WO | WO 2004112747 | A2 * | 12/2004 |
| WO | WO-2005/016246 | | 2/2005 |
| WO | WO-2005/059118 | | 6/2005 |
| WO | WO-2005/072706 | | 8/2005 |
| WO | WO-2005/079854 | | 9/2005 |
| WO | WO-2005/123907 | | 12/2005 |
| WO | WO-2006/080243 | A1 | 8/2006 |
| WO | WO-2007/048326 | | 5/2007 |
| WO | WO-2007/055995 | | 5/2007 |

OTHER PUBLICATIONS

Verpoorte et al., (JBC. 1965;240(3):1156-61).*
Information Hyperlinked Over Proteins (last accessed Sep. 8, 2012) (showing the synonyms for α2-human serum glycoprotein).*
Owens et al., (Int J Pharm. Jan. 3, 2006;307(1):93-102. Epub Nov. 21, 2005).*
ThermoFisher Scientific—Working with Latex Beads. 2 pages. Last accessed Feb. 5, 2016 at www.thermofisher.com/us/en/home/life-science/cell-analysis/qdots-microspheres-nanospheres/idc-surfactant-free-latex-beads/latex-bead-technical-overview/working-with-latex-beads.html.*
ThermoFisher Scientific—Latex Bead Overview. 4 pages. Last accessed Feb. 5, 2016 at www.thermofisher.com/us/en/home/life-science/cell-analysis/qdots-microspheres-nanospheres/idc-surfactant-free-latex-beads/latex-bead-technical-overview.*
Molina-Bolivar et al., (J Macromol Science. Part C—Polymer Reviews, 2005 45:59-98).*
Issekutz et al., The in vivo quantitation and kinetics of monocyte migration into acute inflammatory tissue, Am. J. Pathol., 103:47-55 (1981).
"Dipolar aprotic solvent," IUPAC Compendium of Chemical Terminology, International Union of Pure and Applied Chemistry, 2nd ed. (1997).
Allen et al., "Critical evaluation of acute cardiopulmonary toxicity of microspheres," J. Nucl. Med., 19:1204-1208 (1987).
Aquaro et al., "Macrophages and HIV infection: therapeutical approaches toward this strategic virus reservoir," Antiviral Res., 55:209-225 (2002).
Audran et al., "Fate of mouse macrophages radiolabelled with PKH-95 and injected intravenously," Nucl. Med. Biol., 22:817-21 (1995).
Beduneau et al., "Active targeting of brain tumors using nanocarriers," Biomaterials, 28:4947-67 (2007).
Beduneau et al., "Brain targeting using novel lipid nanovectors," J. Control. Release, 126:44-9 (2008).
Beduneau et al., "Design of targeted lipid nanocapsules by conjugation of whole antibodies and antibody Fab' fragments," Biomaterials, 28:4978-90 (2007).
Beduneau et al., "Facilitated monocyte-macrophage uptake and tissue distribution of superparmagnetic iron-oxide nanoparticles," PLoS ONE, 4:e4343 (12 pp.) (2009).
Beduneau et al., "Human monocyte uptake and carriage of IgG-coated nanoparticles to neuroinflamed brain subregions," Abstract from Nantotech 2008 Conference Program (Boston, Mass.) (May 2008).
Bender et al., "Efficiency of nanoparticles as a carrier for antiviral agents in human immunodeficiency virus-infected human monocytes/macrophases in vitro, antimicrobial agents and chemotherapy," Antimicrob. Agents Chemother., 40:1467-1471 (1996).
Betageri et al., "Fc-receptor-mediated targeting of antibody-bearing liposomes containing dideoxycytidine triphosphate to human monocyte/macrophages," J. Pharm. Pharamcol., 45:48-53 (1993).
Campbell, "Tumor physiology and delivery of nanopharmaceuticals," Anticancer Agents Med. Chem., 6:503-12 (2006).
Carver et al., "Caveolae: mining little caves for new cancer targets," Nat. Rev. Cancer, 3:571-81 (2003).
Choi et al., "A cellular Trojan Horse for delivery of therapeutic nanoparticles into tumors," Nano Lett., 7:3759-65 (2007).
Cibrowski et al., "Human immunodeficiency virus-mononuclear phagocyte interactions: emerging avenues of biomarker discovery, modes of viral persistence and disease pathogenesis," Curr. HIV Res., 4:279-91 (2006).
Connor et al., "Fc receptors for IgG (Fc gamma Rs) on human monocytes and macrophages are not infectivity receptors for human immunodeficiency virus type 1 (HIV-1): studies using bispecific antibodies to target HIV-1 to various myeloid cell surface molecules, including the Fc gamma R," Proc. Natl. Acad. Sci. USA, 88:9593-7 (1991).
Crowe et al., "The contribution of monocyte infection and trafficking to viral persistence, and maintenance of the viral reservoir in HIV infection," J. Leukoc. Biol., 74:635-41 (2003).
Daleke et al., "Endocytosis of liposomes by macrophages: binding, acidification and leakage of liposomes monitored by a new fluorescence assay," Biochim. Biophys. Acta., 1024:352-66 (1990).
Davis et al., "Pulmonary perfusion imaging: acute toxicity and safety factors as a function of particle size," J. Nucl. Med., 19:1209-13 (1978).
Dilworth et al., "Molecular targets for emerging anti-tumor therapies for neurofibromatosis type 1," Biochem. Pharmacol., 72:1485-92 (2006).
Dobrovolskaia et al., "Preclinical studies to understand nanoparticle interaction with the immune system and its potential effects on nanoparticle biodistribution," Mol. Pharm., 5:487-95 (2008).
Dou et al., "Development of a macrophage-based nanoparticle platform for antiretroviral drug delivery," Blood, 108:2827-35 (2006).
Dou et al., "Laboratory investigations for the morphologic, pharmacokinetic, and anti-retroviral properties of indinavir nanoparticles in human monocyte-derived macrophages," Virology, 358:148-58 (2007).
Dutta et al., "Poly (propyleneimine) dendrimer based nanocontainers for targeting of efavirenz to human monocytes/macrophages in vitro," J. Drug Target, 15:89-98 (2007).
Engberink et al., "MRI of monocyte infiltration in an animal model of neuroinflammation using SPIO-labeled monocytes or free USPIO," J. Cereb. Blood Flow Metab., 28:841-51 (2008).
Fischer-Smith et al., "CNS invasion by CD14+/CD16+ peripheral blood-derived monocytes in HIV dementia: perivascular accumulation and reservoir of HIV infection," J. Neurovirol., 7:528-541 (2001).

(56) References Cited

OTHER PUBLICATIONS

Gorantla et al., "Quantitative magnetic resonance and SPECT imaging for macrophage tissue migration and nanoformulated drug delivery," *J. Leukoc. Biol.*, 80:1165-74 (2006).
*Handbook of Pharmaceutical Excipients*, American Pharmaceutical Association and The Pharmaceutical Society of Great Britain, London, England: The Pharmaceutical Press (1986).
Hanemann, "Magic but treatable? Tumours due to loss of merlin," *Brain*, 131:606-15 (2007).
Heiati et al., "Solid lipid nanoparticles as drug carriers: II. Plasma stability and biodistribution of solid lipid nanoparticles containing the lipophilic prodrug 3'-azido-3'-deoxythymidine palmitate in mice," *Int. J. Pharmaceutics*, 174:71-80 (1998).
Holevinsky et al., "Membrane capacitance changes associated with particle uptake during phagocytosis in macrophages," *Biophys. J.*, 75:2577-86 (1998).
Igarashi et al., "Macrophage are the principal reservoir and sustain high virus loads in rhesus macaques after the depletion of CD4+ T cells by a highly pathogenic simian immunodeficiency virus/HIV type 1 chimera (SHIV): implications for HIV-1 infections of humans," *Proc. Natl. Acad. Sci. USA*, 98:658-663 (2001).
Jain et al., "RGD-anchored magnetic liposomes for monocytes/neutrophils-mediated brain targeting," *Int. J. Pharm.*, 261:43-55 (2003).
Kadiu et al., "Mononuclear phagocytes in the pathogenesis of neurodegenerative diseases," *Neurotox. Res.*, 8:25-50 (2005).
Khan et al., "Enhanced anticryptococcal activity of chloroquine in phosphatidylserine-containing liposomes in a murine model," *J. Antimicrob. Chemother.*, 55:223-8 (2005).
Kingsley et al., "Nanotechnology: a focus on nanoparticles as a drug delivery system," *J. Neuroimmune Pharmacol.*, 1:340-50 (2006).
Kinman et al., "Lipid-drug association enhanced HIV-1 protease inhibitor indinavir localization in lymphoid tissues and viral load reduction: a proof of concept study in HIV-2287-infected macaques," *J. Acquir. Immune Defic. Syndr.*, 34:387-397 (2003).
Korf, "Determination of end points for treatment of neurofibromatosis 1," *J. Child Neurol.*, 17:642-645 (2002).
Kuwata et al., "Contribution of monocytes to viral replication in macaques during acute infection with simian immunodeficiency virus," *AIDS Res. Hum. Retroviruses*, 23:372-80 (2007).
Lee et al., "Novel molecular approaches to cystic fibrosis gene therapy," *Biochem. J.*, 387:1-15 (2005).
Limoges et al., "Sustained antiretroviral activity of indinavir nanosuspensions in primary monocyte-derived macrophages," poster presentation, 11th Conference on Retroviruses and Opportunistic Infections, Feb. 8-11, 2004.
Liu et al., "Ingress of blood-borne macrophages across the blood-brain barrier in murine HIV-1 encephalitis," *J. Neuroimmunol.*, 200:41-52 (2008).
Lobenberg et al., "Body distribution of azidothymidine bound to hexyl-cyanoacrylate nanoparticles after i.v. injection to rats," *J. Control Release*, 50:21-30 1998.
Lobenberg et al., "Macrophage targeting of azidothymidine: a promising strategy for AIDS therapy," *AIDS Res. Hum. Retroviruses*, 12:1709-15 (1996).
MacCollin et al., "Establishing priorities in neurofibromatosis research: a workshop summary," *Genetics in Medicine*, 3:212-217 (2001).
Manjunath et al., "Pharmacokinetics, tissue distribution and bioavailability of nitrendipine solid lipid nanoparticles after intravenous and intraduodenal administration," *J. Drug Target*, 14:632-45 (2006).
Margel et al., "Polyacrolein microspheres as a new tool in cell biology," *J. Cell. Sci.*, 56:157-75 (1982).
Mehta et al., "Uptake of liposomes and liposome-encapsulated muramyl dipeptide by human peripheral blood monocytes," *J. Reticuloendothel. Soc.*, 32:155-64 (1982).
Moffat et al., "Management strategies in neurofibromatosis type 2," *Eur. Arch. Otorhinolaryngol.*, 260:12-8 (2003).
Moghimi et al., "Capture of stealth nanoparticles by the body's defences," *Crit. Rev. Ther. Drug Carrier Syst.*, 18:527-50 (2001).
Moghimi et al., "Long-circulating and target-specific nanoparticles: theory to practice," *Pharmacol. Rev.*, 53:283-318 (2001).
Moghimi et al., "Recognition by macrophages and liver cells of opsonized phospholipid vesicles and phospholipid headgroups," *Pharm. Res.*, 18:1-8 (2001).
Moghimi et al., "Stealth liposomes and long circulating nanoparticles: critical issues in pharmacokinetics, opsonization and protein-binding properties," *Prog. Lipid Res.*, 42:463-78 (2003).
Nelson et al., "Coregistration of quantitative proton magnetic resonance spectroscopic imaging with neuropathological and neurophysiological analyses defines the extent of neuronal impairments in murine human immunodeficiency virus type-1 encephalitis," *J. Neurosci. Res.*, 80:562-75 (2005).
Nesbit et al., "In vitro and animal models of human immunodeficiency virus infection of the central nervous system," *Clin. Diagn. Lab. Immunol.*, 9:515-24 (2002).
Nishikawa et al., "Scavenger receptor-mediated uptake and metabolism of lipid vesicles containing acidic phospholipids by mouse peritoneal macrophages," *J. Biol. Chem.*, 265:5226-31 (1990).
Nottet et al., "HIV-1 entry into brain: Mechanisms for the infiltration of HIV-1-infected macrophages across the blood-brain barrier," p. 55, in Gendelman (ed.) et al., *The Neurology of AIDS*, New York: Hodder Arnold Publication (1997).
Oude Engberink et al., "Physicochemical characteristics of pentamidine-loaded polymethacrylate nanoparticles: implication in the intracellular drug release in Leishmania major infected mice," *Radiology*, 243:467-74 (2007).
Owen et al., "Mathematical modelling of the use of macrophages as vehicles for drug delivery to hypoxic tumour sites," *J. Theor. Biol.*, 226:377-91 (2004).
Owens et al., "Opsonization, biodistribution, and pharmacokinetics of polymeric nanoparticles," *Int. J. Pharm.*, 307:93-102 (2006).
Ozawa et al., "A novel means of drug delivery: myoblast-mediated gene therapy and regulatable retroviral vectors," *Annu. Rev. Pharmacol Toxicol.*, 40:295-317 (2000).
Packer et al., "Plexiform neurofibromas in NF1: toward biologic-based therapy," *Neurology*, 58:1461-70 (2002).
Panyam et al., "Rapid endo-lysosomal escape of poly(DL-lactide-co-glycolide) nanoparticles: implications for drug and gene delivery," *FASEB J.*, 16:1217-26 (2002).
Paul et al., "Physicochemical characteristics of pentamidine-loaded polymethacrylate nanoparticles: implication in the intracellular drug release in Leishmania major infected mice," *J. Drug Target*, 5:481-90 (1998).
Pereboeva et al., "Cellular vehicles for cancer gene therapy: current status and future potential," *BioDrugs*, 18:361-85 (2004).
Perno et al., "Relative potency of protease inhibitors in monocytes/macrophages acutely and chronically infected with human immunodeficiency virus," *J. Infect. Dis.*, 178:413-22 (1998).
Perry et al., "Inflammation in the nervous system," *Curr. Opin. Neurobiol.*, 5:636-41 (1995).
Pietruska et al., "Evaluation of mCD14 expression on monocytes and the blood level of sCD14 in patients with generalized aggressive periodontitis," *Adv. Med. Sci.*, 51:166-9 (2006).
Riccardi, "The genetic predisposition to and histogenesis of neurofibromas and neurofibrosarcoma in neurofibromatosis Type 1," *Neurosurg. Focus*, 22:E3 (2007 (11 pages)).
Riemer et al., "Colorimetric ferrozine-based assay for the quantitation of iron in cultured cells," *Anal. Biochem.*, 331:370-5 (2004).
Romberg et al., "Effect of liposome characteristics and dose on the pharmacokinetics of liposomes coated with poly(amino acid)s," *Pharm. Res.*, 24:2394-401 (2007).
Sawchuk et al., "Investigation of distribution, transport and uptake of anti-HIV drugs to the central nervous system," *Adv. Drug Deliv. Rev.*, 39:5-31 (1999).
Schroeder et al., "Physiological effects of subvisible microspheres administered intravenously to beagle dogs," *J. Pharm. Sci.*, 67:508-13 (1978).
Solas et al., "Discrepancies between protease inhibitor concentrations and viral load in reservoirs and sanctuary sites in human immunodeficiency virus-infected patients," *Antimicrob. Agents Chemother.*, 47:238-43 (2003).

(56) References Cited

OTHER PUBLICATIONS

Spitzenberger et al., "Novel delivery system enhances efficacy of antiretroviral therapy in animal model for HIV-1 encephalitis," *J. Cereb. Blood Flow Metab.*, 27:1033-42 (2007).

Thiele et al., "Evaluation of particle uptake in human blood monocyte-derived cells in vitro. Does phagocytosis activity of dendritic cells measure up with macrophages?", *J. Control. Release*, 76:59-71 (2001).

Von Briesen et al., "Controlled release of antiretroviral drugs," *AIDS Rev.*, 2:31-8 (2000).

Watts et al., "Endocytosis: what goes in and how?," *J. Cell. Sci.*, 103:1-8 (1992).

Yokel et al., "Acute toxicity of latex microspheres," *Toxicol. Lett.*, 9:165-70 (1981).

Zarnitsyn et al., "Physical parameters influencing optimization of ultrasound-mediated DNA transfection," *Ultrasound in Med. & Biol.*, 30:527-38 (2004).

Zelivyanskaya et al., "Tracking superparamagnetic iron oxide labeled monocytes in brain by high-field magnetic resonance imaging," *J. Neurosci. Res.*, 73:284-95 (2003).

Zhu et al., "Evidence for human immunodeficiency virus type 1 replication in vivo in CD14(+) monocytes and its potential role as a source of virus in patients on highly active antiretroviral therapy," *J. Virol.*, 76:707-16 (2002).

Thiele et al., Competitive adsorption of serum proteins at microparticles affects phagocytosis by dendritic cells, *Biomaterials*, 24:1409-18 (2003).

Written Opinion of the International Preliminary Examining Authority for corresponding International Application No. PCT/US09/36185 (dated Mar. 26, 2010).

International Preliminary Report on Patentability for corresponding International Application No. PCT/US2009/036185, dated Jun. 25, 2010.

International Search Report and Written Opinion for corresponding International Application No. PCT/US2009/036185, dated Jul. 2, 2009.

Munerati et al., Macrophages loaded with doxorubicin by ATP-mediated permeabilization: potential carriers for antitumor therapy, *Biochimica et Biophysicia Acta*, 1224:269-76 (1994).

Soma et al., Investigation of the role of macrophages on the cytotoxicity of doxorubicin and doxorubicin-loaded nanoparticles on M5076 cells in vitro, *J. Controlled Release*, 68:281-9 (2000).

Coester et al., Preparation of avidin-labelled gelatin nanoparticles as carriers for biotinylated peptide nucleic acid (PNA), *Int. J. Pharm.*, 196:147-9 (2000).

D'Souza et al., Site specific microencapsulated drug targeting strategies—liver and gastro-intestinal tract targeting, *Adv. Drug Delivery Rev.*, 17:247-54 (1995).

Kreuter, Nanoparticulate systems for brain delivery of drugs, *Adv. Drug Deliv. Rev.*, 47:65-81 (2001).

Mishra et al., Engineered human erythrocytes as carriers for ciprofloxacin, *Drug Delivery*, 3:239-44 (1996).

Mishra et al., Surface modified methotrexate loaded erythrocytes for enhanced macrophage uptake, *J. Drug Target*, 8:217-24 (2000).

Ginsburg et al. "Role of leukocyte factors and cationic polyelectrolytes in phagocytosis of group A Streptococci and *Candida albicans* by neutrophils, macrophages, fibroblasts and epithelial cells: Modulation by anionic polyelectrolytes in relation to pathogenesis of chronic inflammation", *Inflammation*, 5: 289-312 (1981).

Bian et al., "Direct technetium-99m labeling of anti-hepatoma monoclonal antibody fragment: a radioimmunoconjugate for hepatocellular carcinoma imaging", *World J. Gastroentero.*, 6(3): 348-52 (2000).

Dou et al., Macrophage delivery of nanoformulated antiretroviral drug to the brain in a murine model of neuroAIDS, *J. Immunol.*, 183:611-9 (2009).

Nowacek et al., NanoART synthesis, characterization, uptake, release and toxicology for human monocyte-macrophage drug delivery, *Nanomedicine*, 4:903-17 (2009).

\* cited by examiner

COMPOSITIONS AND METHODS FOR DRUG DELIVERY

CROSS REFERENCE TO RELATED APPLICATION

This application claims the priority benefits of U.S. Patent Application Ser. No. 61/068,151 filed Mar. 5, 2008, U.S. Patent Application Ser. No. 61/205,259 filed Jan. 20, 2009, and U.S. Patent Application Ser. No. 61/148,917 filed Jan. 30, 2009, the disclosures of which are hereby incorporated by reference.

GOVERNMENT RIGHTS IN THE INVENTION

This invention was made with government support under Grant No. R01NS036126-12 awarded by the National Institutes of Health. The government has certain rights in the invention.

BACKGROUND

1. Field of the Disclosure

The disclosure relates generally to compositions comprising coated particles and to methods of making and using such compositions for targeted drug delivery.

2. Brief Description of Related Technology

Nanoparticles (including nanospheres) and microparticles (including microspheres) referred to herein collectively as "particles," are solid or semi-solid particles having a diameter from about 1 nm to about 10,000 nm (10 microns). Such particles can be formed from a variety of materials, including proteins, synthetic polymers, polysaccharides, nucleic acids, small molecules, and combinations thereof, and have been used in many different applications, primarily separations, diagnostics, and drug delivery.

Compositions comprising such particles have been found to be useful for drug delivery. For example, U.S. Patent Publication No. 2006/0073199 discloses that particles comprising an active agent can be formulated as aqueous suspensions, and stabilized against aggregation and particle growth by providing surfactant coatings on or about the particles.

There is an on-going need for development of compositions comprising particles and methods for making and using same, particularly in delivering drugs of interest.

SUMMARY

One aspect of the invention is directed to a surface-modified particle comprising a particle core and a coating associated with the particle core. The particle core comprises an active agent, such as a therapeutic agent or a diagnostic agent (e.g., a small organic molecule or a biomacromolecule). The coating comprises an opsonin, for example, an antibody having an isotype of IgG or a complement protein such as C3b and C5. Other proteins known to act as opsonins also can be used. The surface-modified particles according to the present invention generally have an average size from about 1 nm to about 10,000 nm.

Another aspect of the invention is directed to a method of enhancing cellular uptake of an active agent. The method comprises contacting cells with surface-modified particles under conditions sufficient to enhance cellular uptake of the surface-modified particles. The particles comprise a particle core and a coating associated with the particle core, wherein the particle core comprises an active agent, the coating comprises an opsonin (e.g., an antibody having an isotype of IgG or a complement protein such as C3b or C5), and the surface-modified particle has an average size from about 1 nm to about 2,000 nm.

Another aspect of the invention is directed to a method for treating a subject having an inflammatory disease or disorder comprising administering to said subject a plurality of surface-modified particles, said surface-modified particles comprising a particle core and a coating associated with the particle core, wherein the particle core comprises an active agent (e.g., an anti-inflammatory agent), the coating comprises an opsonin (e.g., an antibody having an isotype of IgG or a complement protein such as C3b or C5), the surface-modified particle has an average size from about 1 nm to about 2,000 nm, and said administration is effective in alleviating, treating, and/or preventing symptoms or pathologies associated with said inflammatory disease or disorder.

Another aspect of the invention is directed to a method for treating a subject having a proliferative disease or disorder comprising administering to said subject a plurality of surface-modified particles, said surface-modified particles comprising a particle core and a coating associated with the particle core, wherein the particle core comprises an active agent (e.g., an anti-proliferative such as an antineoplastic agent), the coating comprises an opsonin (e.g., an antibody having an isotype of IgG or a complement protein such as C3b or C5), the surface-modified particle has an average size from about 1 nm to about 2,000 nm, and said administration is effective in alleviating, treating, and/or preventing symptoms or pathologies associated with said proliferative disease or disorder.

Another aspect of the invention is directed to a method for treating a subject having an infectious disease or disorder comprising administering to said subject a plurality of surface-modified particles, said surface-modified particles comprising a particle core and a coating associated with the particle core, wherein the particle core comprises an active agent (e.g., an anti-infective agent), the coating comprises an opsonin (e.g., an antibody having an isotype of IgG or a complement protein such as C3b or C5), the surface-modified particle has an average size from about 1 nm to about 2,000 nm, and said administration is effective in alleviating, treating, and/or preventing symptoms or pathologies associated with said infectious disease or disorder.

In another aspect, the invention is directed to a method for treating a subject having a neurodegenerative disease or disorder comprising administering to said subject a plurality of surface-modified particles, said surface-modified particles comprising a particle core and a coating associated with the particle core, wherein the particle core comprises an active agent (e.g., an anti-neurodegenerative agent), the coating comprises an opsonin (e.g., an antibody having an isotype of IgG or a complement protein such as C3b or C5), the surface-modified particle has an average size from about 1 nm to about 2,000 nm, and said administration is effective in alleviating, treating, and/or preventing symptoms or pathologies associated with said neurodegenerative disease or disorder.

DETAILED DESCRIPTION

Figure 1:
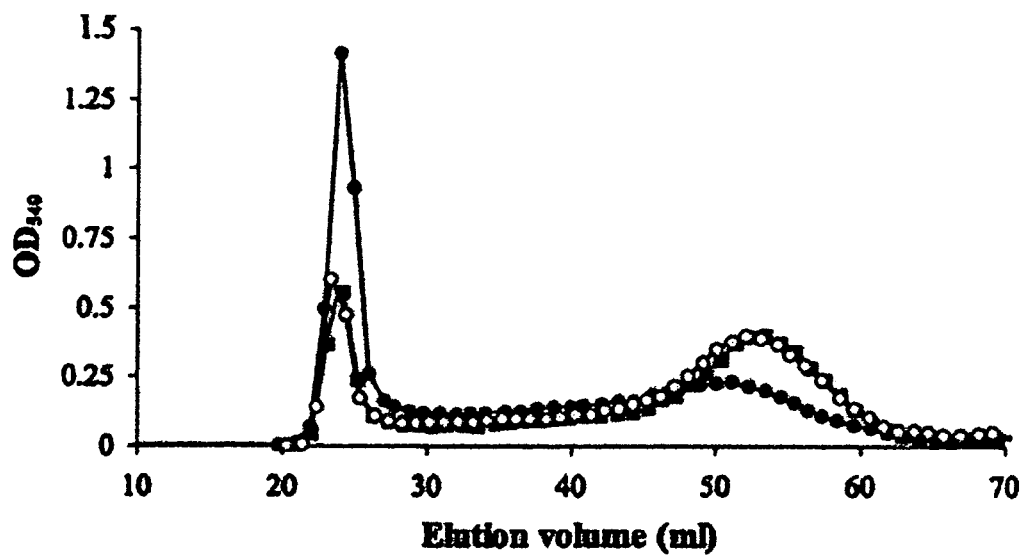
FIG. 1 is a graph showing elution profiles of various superparamagnetic iron oxide (SPIO) nanoparticles (NP) from a Sepharose 4B-CL column. Shown are IgG-conjugated SPIO NP (IgG-SPIO) after incubation of IgG with oxidized SPIO (closed circles); IgG incubated with non-oxidized SPIO (closed squares); and oxidized SPIO blocked by addition of an excess of amine groups (open circles).

The claimed invention is susceptible of embodiments in many different forms. Preferred embodiments, as disclosed herein, are to be considered exemplary of the principles of the claimed invention and thus not intended to limit the broad aspects of the claimed invention to the embodiments illustrated.

One aspect of the invention provides a surface-modified particle comprising a particle core and a coating associated with the particle core. The particle core comprises an active agent, the coating comprises an opsonin (e.g., an antibody having an isotype of IgG or a complement protein such as C3b or C5), and the surface-modified particle has an average size from about 1 nm to about 2,000 nm. In some embodiments, particles having coatings comprising complement proteins can be used in combination with substances capable of attenuating the effects of histamine release, which can be induced by activated complement proteins.

Another aspect of the present invention provides methods for enhancing uptake of an active agent by phagocytic or non-phagocytic cells by exposing the cells to a surface-modified particle comprising a particle core and a coating associated with the particle core. The particle core comprises an active agent, the coating comprises an opsonin (e.g., an antibody having an isotype of IgG or a complement protein such as C3b or C5), and the surface-modified particle has an average size from about 1 nm to about 2,000 nm. Enhanced uptake by the cells of the active agent is observed as compared to cells contacted with particles not having a coating comprising an opsonin.

In yet another aspect, the invention also provides methods for delivery of a surface-modified particle to a target tissue of a mammalian subject through cellular transport. As used herein, "target tissue" or "tissue target" refers to the particular tissue of mammal to be treated. Examples of such target tissues include, but are not limited to, the brain and other portions of the central nervous system, the lymphatic system, the liver, and any site of infection, inflammation, or tumor.

For example, in one aspect, the invention contemplates methods and compositions for treating a subject having an inflammatory disease or disorder comprising administering to said subject a plurality of surface-modified particles, said surface-modified particles comprising a particle core and a coating associated with the particle core, wherein the particle core comprises an active agent, the coating comprises an opsonin (e.g., an antibody having an isotype of IgG or a complement protein such as C3b or C5), the surface-modified particle has an average size from about 1 nm to about 2,000 nm, and said administration is effective in alleviating, treating, and/or preventing symptoms or pathologies associated with said inflammatory disease or disorder. In one aspect, the active agent is an anti-inflammatory agent.

In another aspect, the invention contemplates methods and compositions for treating a subject having a neurodegenerative disease or disorder comprising administering to said subject a plurality of surface-modified particles, said surface-modified particles comprising a particle core and a coating associated with the particle core, wherein the particle core comprises an active agent, the coating comprises an opsonin (e.g., an antibody having an isotype of IgG or a complement protein such as C3b or C5), the surface-modified particle has an average size from about 1 nm to about 2,000 nm, and said administration is effective in alleviating, treating, and/or preventing symptoms or pathologies associated with said neurodegenerative disease or disorder. In one aspect, the active agent is an anti-neurodegenerative agent.

In yet another aspect, the invention contemplates methods and compositions for treating a subject having an proliferative disease or disorder comprising administering to said subject a plurality of surface-modified particles, said surface-modified particles comprising a particle core and a coating associated with the particle core, wherein the particle core comprises an active agent, the coating comprises an opsonin (e.g., an antibody having an isotype of IgG or a complement protein such as C3b or C5), the surface-modified particle has an average size from about 1 nm to about 2,000 nm, and said administration is effective in alleviating, treating, and/or preventing symptoms or pathologies associated with said proliferative disease or disorder. In one aspect, the active agent is an anti-proliferative agent such as an antineoplastic agent.

In a still further aspect, the invention contemplates methods and compositions for treating a subject having an infectious disease or disorder comprising administering to said subject a plurality of surface-modified particles, said surface-modified particles comprising a particle core and a coating associated with the particle core, wherein the particle core comprises an active agent, the coating comprises an opsonin (e.g., an antibody having an isotype of IgG or a complement protein such as C3b or C5), the surface-modified particle has an average size from about 1 nm to about 2,000 nm, and said administration is effective in alleviating, treating, and/or preventing symptoms or pathologies associated with said infectious disease or disorder. In one aspect, the active agent is an anti-infective agent such as an anti-fungal agent, an anti-viral agent, an anti-bacterial agent, or an anti-parasitic agent.

Thus, the methods of administration disclosed herein contemplate administration of a therapeutically effective amount of said surface modified particles. As used herein, the term "therapeutically effective amount" refers to an amount of surface-coated particles that is sufficient to alleviate, ameliorate, clear, treat, and/or prevent symptoms or pathologies associated with a disease or disorder contemplated for treatment in accordance with the treatment methods disclosed herein.

As used herein, the term "opsonin" refers to proteins or peptides that bind to particles or cells, thereby increasing the susceptibility of said particle or cell to phagocytosis. Fragments of known opsonins having biological activity comparable to the corresponding full-length opsonin are considered to be opsonins, as used herein. For example, fragments of IgG typically include a fragment sufficient to bind a phagocyte. Such fragments can further include sufficient hydrophobic moieties to non-covalently associate with a hydrophobic particle surface, as described herein. Suitable IgG fragments include, for example, IgG-Fab fragments and IgG-Fc fragments. Similarly, opsonin mimetics also are considered to be opsonins, as used herein. As used herein, "opsonin mimetics" refer to compounds (including peptides) having biological activity comparable to an opsonin or that mimics the activity of the opsonin. A person of ordinary skill can easily determine whether a moiety is an opsonin mimetic in view of the opsonin's known biological activity.

The following description of the surface-modified particle typically applies to all embodiments disclosed herein. The active agent of the surface-modified particle can be poorly water soluble or water soluble. The active agent can be a therapeutic agent or a diagnostic agent. Active agents used in accordance with the compositions and methods disclosed herein exhibit the pharmaceutical activities normally associated with such active agents even though the active agents are taken up and subsequently delivered by phagocytic or non-phagocytic cells.

The active agent can be selected from a variety of known pharmaceutical compounds such as, but not limited to: analgesics, anesthetics, analeptics, adrenergic agents, adrenergic blocking agents, adrenolytics, adrenocorticoids, adrenomimetics, anticholinergic agents, anticholinesterases, anticonvulsants, alkylating agents, alkaloids, allosteric inhibitors, anabolic steroids, anorexiants, antacids, antidiarrheals, antidotes, antifolics, antipyretics, antirheumatic agents, psychotherapeutic agents, antihelmintics, anticoagulants, antidepressants, antiepileptics, anti-infective agents (e.g., antifungals, antiviral agents such as antiretroviral agents, and antibiotics), antihistamines, antimuscarinic agents, antimycobacterial agents, antineoplastic agents, antiprotozoal agents, anxiolytic sedatives, beta-adrenoceptor blocking agents, corticosteroids, cough suppressants, dopaminergics, hemostatics, hematological agents, hypnotics, immunological agents, muscarinics, parasympathomimetics, prostaglandins, radio-pharmaceuticals, sedatives, stimulants, sympathomimetics, vitamins, xanthines, growth factors, hormones, and antiprion agents.

Examples of antineoplastic agents include, but are not limited to, paclitaxel, paclitaxel derivative compounds, alkaloids, antimetabolites, enzyme inhibitors, alkylating agents, and combinations thereof.

The active agent also can be a protease inhibitor, such as an HIV protease inhibitor. Examples of protease inhibitors include, but are not limited to, indinavir, ritonavir, saquinavir, nelfinavir, and combinations thereof.

The active agent can be a nucleoside reverse transcriptase inhibitor. Examples of nucleoside reverse transcriptase inhibitors include, but are not limited to, zidovudine, didanosine, stavudine, zalcitabine, lamivudine, and combinations thereof.

The active agent can be a non-nucleoside reverse transcriptase inhibitor. Examples of non-nucleoside reverse transcriptase inhibitors include, but are not limited to, efavirenz, nevirapine, delaviradine, and combinations thereof.

Examples of anti-inflammatory agents include, but are not limited to, non-steroidal anti-inflammatory drugs, non-selective cycloxygenase (COX) inhibitors, COX-1 inhibitors, COX-2 inhibitors, lipoxygenase inhibitors, corticosteroids, anti-oxidants, tumor necrosis factor (TNF) inhibitors, and combinations thereof. Examples of COX-2 inhibitors include, but are not limited to, celecoxib, rofecoxib, valdecoxib, parecoxib, lumiracoxib, etoricoxib, and combinations thereof.

Diagnostic agents include x-ray imaging agents and contrast media. Examples of x-ray imaging agents include WIN-8883 (ethyl 3,5-diacetamido-2,4,6-triiodobenzoate) also known as the ethyl ester of diatrazoic acid (EEDA), WIN 67722, i.e., (6-ethoxy-6-oxohexyl-3,5-bis(acetamido)-2,4,6-triiodobenzoate; ethyl-2-(3,5-bis(acetamido)-2,4,6-triiodobenzoyloxy) butyrate (WIN 16318); ethyl diatrizoxyacetate (WIN 12901); ethyl 2-(3,5-bis(acetamido)-2,4,6-triiodobenzoyloxy)propionate (WIN 16923); N-ethyl 2-(3,5-bis(acetamido)-2,4,6-triiodobenzoyloxy acetamide (WIN 65312); isopropyl 2-(3,5-bis(acetamido)-2,4,6-triiodobenzoyloxy) acetamide (WIN 12855); diethyl 2-(3,5-bis(acetamido)-2,4,6-triiodobenzoyloxy) malonate (WIN 67721); ethyl 2-(3,5-bis(acetamido)-2,4,6-triiodobenzoyloxy)phenylacetate (WIN 67585); propanedioic acid, [[3,5-bis(acetylamino)-2,4,5-triodobenzoyl]oxy]bis(1-methyl)ester (WIN 68165); and benzoic acid, 3,5-bis(acetylamino)-2,4,6-triiodo-4-(ethyl-3-ethoxy-2-butenoate) ester (WIN 68209). Contrast agents include those that are expected to disintegrate relatively rapidly under physiological conditions, thus minimizing any particle associated inflammatory response. Disintegration can result from enzymatic hydrolysis, solubilization of carboxylic acids at physiological pH, or other mechanisms. Thus, poorly soluble iodinated carboxylic acids such as iodipamide, diatrizoic acid, and metrizoic acid, along with hydrolytically labile iodinated species such as WIN 67721, WIN 12901, WIN 68165, and WIN 68209 are included.

Other contrast media include, but are not limited to, particulate preparations of magnetic resonance imaging aids such as gadolinium chelates, or other paramagnetic contrast agents. Examples of such compounds are gadopentetate dimeglumine (MAGNEVIST®) and gadoteridol (PROHANCE®).

A description of classes of therapeutic agents and diagnostic agents and a listing of species within each class can be found in Martindale, The Extra Pharmacopoeia, 31st Edition, The Pharmaceutical Press, London, 1996 which is incorporated herein by reference and made a part hereof. The listed therapeutic agents and diagnostic agents are commercially available and/or can be prepared by known techniques.

In a specific embodiment, the active agent is a poorly water-soluble compound. What is meant by "poorly water soluble" is a solubility of the compound in water of less than about 10 mg/mL, and preferably less than about 1 mg/mL. These poorly water-soluble compounds are particularly suitable for aqueous suspension preparations since there are limited alternatives of formulating these compounds in an aqueous medium. Advantageously, opsonins such as IgG, which provide the coatings in accordance with the invention, can adsorb to the surface of particles comprising such poorly water soluble active agents to form a substantially uniform coating thereon. For example, the hydrophobic tail moieties of opsonins such as IgG are able to associate with hydrophobic regions on the particle surface. In addition, opsonins such as IgG are positively charged when the pH is below the isoelectric point for the opsonin, and thus a strong electrostatic interaction between the opsonin and the hydrophobic particle (which can be negatively charged) can stabilize the coating comprising the opsonin protein. Alternatively, opsonins such as IgG are negatively charged when the pH is above the isoelectric point for the opsonin, and thus a strong electrostatic interaction between the opsonin and the hydrophobic particle (which can also be positively charged) can stabilize the coating comprising the opsonin protein. In one preferred aspect, the poorly water soluble active agent compound is an organic compound having a molecular weight less than 2500 grams/mol, less than 2000 grams/mol, and most typically less than 1000 grams/mol, for example, between 200 grams/mol and 900 grams/mol. Such organic compounds are sometimes referred to as "small molecules."

Alternatively, the invention can be practiced with water-soluble compounds. These water soluble active compounds can be entrapped in a solid carrier matrix (for example, poly-lactate-polyglycolate copolymer, albumin, starch), or encapsulated in a surrounding vesicle that is substantially impermeable to the active agent. This encapsulating vesicle can be a polymeric coating such as polyacrylate. Further, the small particles prepared from these water soluble compounds can be modified to improve chemical stability and control the pharmacokinetic properties of the compounds by controlling the release of the compounds from the particles. Examples of water-soluble compounds include, but are not limited to, simple organic compounds, proteins, peptides, nucleotides, oligonucleotides, and carbohydrates.

The following description of particles also applies to all embodiments disclosed herein. The particles can be amorphous, semicrystalline, crystalline, or a combination thereof as determined by suitable analytical methods such as differential scanning calorimetry (DSC) or X-ray diffraction. Prior to administration, the particles can be homogenized through a homogenization process. The particles can also be homogenized through a microprecipitation/homogenization process.

The coated particles generally have an average effective particle size of generally from about 1 nm to about 2 µm (or 2000 nanometers) as measured by dynamic light scattering methods (e.g., photocorrelation spectroscopy, laser diffraction, low-angle laser light scattering (LALLS), medium-angle laser light scattering (MALLS)), light obscuration methods (Coulter method, for example), rheology, or microscopy (light or electron). The preferred average effective particle size depends on factors such as the intended route of administration, formulation, solubility, toxicity and bioavailability of the compound. Other suitable particle sizes include, but are not limited to, about 10 nm to about 1 µm, about 50 nm to about 500 nm, and/or about 100 nm to about 250 nm.

Preparation of the Particle Core

The processes for preparing the particles used in the present invention can be accomplished through numerous techniques. A representative, but non-exhaustive, discussion of techniques for preparing particles follows.

I. Energy Addition Techniques for Forming Small Particle Dispersions

In general, the method of preparing small particle dispersions using energy addition techniques includes the step of adding the active agent or pharmaceutically active compound, which sometimes shall be referred to as a drug, in bulk form to a suitable vehicle such as water or aqueous solution generally containing one or more of the surfactants set forth below, or other liquid in which the pharmaceutical compound is not appreciably soluble, to form a first suspension, which shall be referred to as a presuspension. Energy is added to the presuspension to form a particle dispersion which is physically more stable than the presuspension. Energy is added by mechanical grinding (e.g., pearl milling, ball milling, hammer milling, fluid energy milling, jet milling, or wet grinding). Such techniques are disclosed in U.S. Pat. No. 5,145,684, which is incorporated herein by reference and made a part hereof.

Energy addition techniques further include subjecting the presuspension to high shear conditions including cavitation, shearing or impact forces utilizing a microfluidizer. The present invention further contemplates adding energy to the presuspension using a piston gap homogenizer or counter current flow homogenizer such as those disclosed in U.S. Pat. No. 5,091,188 which is incorporated herein by reference and made a part hereof. Suitable piston gap homogenizers are commercially available under the product names EMULSIFLEX™ (Avestin) and FRENCH® Pressure Cell (Thermo Spectronic). Suitable microfluidizers are available from Microfluidics Corp.

The step of adding energy can also be accomplished using sonication techniques. The step of sonicating can be carried out with any suitable sonication device. Suitable devices include Branson Model S-450A and Cole-Parmer 500/750 Watt Model. Such devices are well known in the industry. Typically the sonication device has a sonication horn or probe that is inserted into the presuspension to emit sonic energy into the solution. The sonicating device, in a preferred form of the invention, is operated at a frequency of from about 1 kHz to about 90 kHz and more preferably from about 20 kHz to about 40 kHz or any range or combination of ranges therein. The probe sizes can vary and preferably are in distinct sizes such as ½ inch or ¼ inch or the like.

The dispersion of small particles can be sterilized prior to administering. Sterilization can be accomplished by heat sterilization, gamma irradiation, filtration (either directly as a dispersion having particle sizes under 200 nm, or by sterile filtration of the solutions used in the precipitation process, prior to forming the solid dispersion), and by application of very high pressure (greater than 2000 atmospheres), or by a combination of high pressure and elevated temperature.

II. Precipitation Methods for Preparing Submicron Sized Particle Dispersions

Small particle dispersions can also be prepared by precipitation techniques. The following is a description of examples of precipitation techniques.

Microprecipitation Methods.

One example of a microprecipitation method is disclosed in U.S. Pat. No. 5,780,062, which is incorporated herein by reference and made a part hereof. The '062 patent discloses an organic compound precipitation process including: (i) dissolving the organic compound in a water-miscible first solvent; (ii) preparing a solution of polymer and an amphiphile in an aqueous second solvent and in which second solvent the organic compound is substantially insoluble whereby a polymer/amphiphile complex is formed; and (iii) mixing the solutions from steps (i) and (ii) so as to cause precipitation of an aggregate of the organic compound and the polymer/amphiphile complex.

Other suitable precipitation processes are disclosed in U.S. Pat. Nos. 6,607,784, 7,037,528, 6,869,617, 6,884,436, which are incorporated herein by reference and made a part hereof. The processes disclosed include the steps of: (1) dissolving an organic compound in a water miscible first organic solvent to create a first solution; (2) mixing the first solution with a second solvent or water to precipitate the organic compound to create a presuspension; and (3) adding energy to the presuspension in the form of high-shear mixing or heat to provide a dispersion of small particles. Optionally, the first organic solvent is removed from the mixture by any suitable means such as centrifugation or filtration methods. Moreover, the continuous phase of the dispersion can be optionally replaced by another continuous phase by removing the first continuous phase using methods such as centrifugation and filtration, and adding a second continuous phase and subsequently redispersing the solid material in the second continuous phase. One or more optional surfactants set forth below can be added to the first organic solvent or the second aqueous solution.

Emulsion Precipitation Methods.

One suitable emulsion precipitation technique is disclosed in U.S. Patent Pub. No. 2005/0037083, which is incorporated herein by reference and is made a part hereof. In this approach, the process includes the steps of: (1) providing a multiphase system having an organic phase and an aqueous phase, the organic phase having a pharmaceutically active compound therein; and (2) sonicating the system to evaporate a portion of the organic phase to cause precipitation of the compound in the aqueous phase to form a dispersion of small particles. The step of providing a multiphase system includes the steps of: (1) mixing a water immiscible solvent with the pharmaceutically active compound to define an organic solution, (2) preparing an aqueous based solution with one or more surface active compounds, and (3) mixing the organic solution with the aqueous solution to form the multiphase system. The step of mixing the organic phase and the aqueous phase can include the use of piston gap homogenizers, colloidal mills, high speed stirring equipment, extrusion equipment, manual agitation or shaking equipment, microfluidizer, or other equipment or techniques for providing high shear conditions. The crude emulsion will have oil droplets in the water of a size of approximately less than 1 μm in diameter. The crude emulsion is sonicated to define a microemulsion and eventually to provide a dispersion of small particles.

Another approach to preparing a dispersion of small particles is disclosed U.S. Pat. No. 6,835,396, which is incorporated herein by reference and made a part hereof. The process includes the steps of: (1) providing a crude dispersion of a multiphase system having an organic phase and an aqueous phase, the organic phase having a pharmaceutical compound therein; (2) providing energy to the crude dispersion to form a fine dispersion; (3) freezing the fine dispersion; and (4) lyophilizing the fine dispersion to obtain small particles of the pharmaceutical compound. The small particles can be sterilized by the techniques set forth below or the small particles can be reconstituted in an aqueous medium and sterilized.

The step of providing a multiphase system includes the steps of: (1) mixing a water immiscible solvent with the pharmaceutically effective compound to define an organic solution; (2) preparing an aqueous based solution with one or more surface active compounds; and (3) mixing the organic solution with the aqueous solution to form the multiphase system. The step of mixing the organic phase and the aqueous phase includes the use of piston gap homogenizers, colloidal mills, high speed stirring equipment, extrusion equipment, manual agitation or shaking equipment, microfluidizer, or other equipment or techniques for providing high shear conditions.

Solvent-Antisolvent Precipitation. Small particle dispersions can also be prepared using a solvent-antisolvent precipitation technique disclosed by Fessi et al. in U.S. Pat. No. 5,118,528 and by Leclef et al. in U.S. Pat. No. 5,100,591 which are incorporated herein by reference and made a part hereof. Both processes include the steps of: (1) preparing a liquid phase of a biologically active substance in a solvent or a mixture of solvents to which may be added one or more surfactants; (2) preparing a second liquid phase of a non-solvent or a mixture of non-solvents, the non-solvent is miscible with the solvent or mixture of solvents for the substance; (3) adding together the solutions of (1) and (2) with stirring; and (4) removing of unwanted solvents to produce a dispersion of small particles. These methods are distinguished from those described under the above section, "Microprecipitation Methods", in that they do not provide for a last step of adding energy to the suspension in the form of high-shear mixing or heat.

Phase Inversion Precipitation.

Small particle dispersions can be formed using phase inversion precipitation as disclosed in U.S. Pat. Nos. 6,235,224, 6,143,211 and 6,616,869, each of which is incorporated herein by reference and made a part hereof. Phase inversion is a term used to describe the physical phenomena by which a polymer dissolved in a continuous phase solvent system inverts into a solid macromolecular network in which the polymer is the continuous phase. One method to induce phase inversion is by the addition of a nonsolvent to the continuous phase. The polymer undergoes a transition from a single phase to an unstable two phase mixture: polymer rich and polymer poor fractions. Micellar droplets of nonsolvent in the polymer rich phase serve as nucleation sites and become coated with polymer. The '224 patent discloses that phase inversion of polymer solutions under certain conditions can bring about spontaneous formation of discrete microparticles, including nanoparticles. The '224 patent discloses dissolving or dispersing a polymer in a solvent. A pharmaceutical agent is also dissolved or dispersed in the solvent. For the crystal seeding step to be effective in this process, it is desirable the agent is dissolved in the solvent. The polymer, the agent and the solvent together form a mixture having a continuous phase, wherein the solvent is the continuous phase. The mixture is then introduced into at least tenfold excess of a miscible nonsolvent to cause the spontaneous formation of the microencapsulated microparticles of the agent having an average particle size of between 10 nm and 10 μm. The particle size is influenced by the solvent:nonsolvent volume ratio, polymer concentration, the viscosity of the polymer-solvent solution, the molecular weight of the polymer, and the characteristics of the solvent-nonsolvent pair.

pH Shift Precipitation.

Small particle dispersions can be formed by pH shift precipitation techniques. Such techniques typically include a step of dissolving a drug in a solution having a pH where the drug is soluble, followed by the step of changing the pH to a point where the drug is no longer soluble. The pH can be acidic or basic, depending on the particular pharmaceutical compound. The solution is then neutralized to form a dispersion of small particles. One suitable pH shifting precipitation process is disclosed in U.S. Pat. No. 5,665,331, which is incorporated herein by reference and made a part hereof. The process includes the step of dissolving of the pharmaceutical agent together with a crystal growth modifier (CGM) in an alkaline solution and then neutralizing the solution with an acid in the presence of suitable surface-modifying surface-active agent or agents to form a small particle dispersion of the pharmaceutical agent. The precipitation step can be followed by steps of diafiltration clean-up of the dispersion and then adjusting the concentration of the dispersion to a desired level.

Other examples of pH shifting precipitation methods are disclosed in U.S. Pat. Nos. 5,716,642; 5,662,883; 5,560,932; and 4,608,278, which are incorporated herein by reference and are made a part hereof.

Infusion Precipitation Method.

Suitable infusion precipitation techniques to form small particle dispersions are disclosed in U.S. Pat. Nos. 4,997,454 and 4,826,689, which are incorporated herein by reference and made a part hereof. First, a suitable solid compound is dissolved in a suitable organic solvent to form a solvent mixture. Then, a precipitating nonsolvent miscible with the organic solvent is infused into the solvent mixture at a temperature between about −10° C. and about 100° C. and at an infusion rate of from about 0.01 ml per minute to about 1000 ml per minute per volume of 50 ml to produce a suspension of precipitated non-aggregated solid particles of the compound with a substantially uniform mean diameter of less than 10 μm. Agitation (e.g., by stirring) of the solution being infused with the precipitating nonsolvent is preferred. The nonsolvent may contain a surfactant to stabilize the particles against aggregation. The particles are then separated from the solvent. Depending on the solid compound and the desired particle size, the parameters of temperature, ratio of nonsolvent to solvent, infusion rate, stir rate, and volume can be varied according to the invention. The particle size is proportional to the ratio of nonsolvent:solvent volumes and the temperature of infusion and is inversely proportional to the infusion rate and the stirring rate. The precipitating nonsolvent may be aqueous or non-aqueous, depending upon the relative solubility of the compound and the desired suspending vehicle.

Temperature Shift Precipitation.

Temperature shift precipitation techniques may also be used to form small particle dispersions. This technique is disclosed in U.S. Pat. No. 5,188,837, which is incorporated herein by reference and made a part hereof. In an embodiment of the invention, lipospheres are prepared by the steps of: (1) melting or dissolving a substance such as a drug to be delivered in a molten vehicle to form a liquid of the substance to be delivered; (2) adding a phospholipid along with an aqueous medium to the melted substance or vehicle at a temperature higher than the melting temperature of the substance or vehicle; (3) mixing the suspension at a temperature above the melting temperature of the vehicle until a homogenous fine preparation is obtained; and then (4) rapidly cooling the preparation to room temperature or below.

Solvent Evaporation Precipitation.

Solvent evaporation precipitation techniques are disclosed in U.S. Pat. No. 4,973,465 which is incorporated herein by reference and made a part hereof. The '465 patent discloses methods for preparing microcrystals including the steps of: (1) providing a solution of a pharmaceutical composition and a phospholipid dissolved in a common organic solvent or combination of solvents, (2) evaporating the solvent or solvents and (3) suspending the film obtained by evaporation of the solvent or solvents in an aqueous solution by vigorous stirring to form a dispersion of small particles. The solvent can be removed by evaporating a sufficient quantity of the solvent to cause precipitation of the compound. The solvent can also be removed by other well known techniques such as applying a vacuum to the solution or blowing nitrogen over the solution.

Reaction Precipitation.

Reaction precipitation includes the steps of dissolving the pharmaceutical compound, and optionally other excipients, into a suitable solvent to form a solution. The compound may be added in an amount at or below the saturation point of the compound in the solvent. The compound or any of the excipients is precipitated from solution by reacting with a chemical agent or by modification in response to adding energy such as heat or UV light or the like such that the modified compound has a lower solubility in the solvent and precipitates from the solution to form a small particle dispersion. Precipitation of excipient provides a solid matrix into which the drug is sorbed.

Compressed Fluid Precipitation.

A suitable technique for precipitating by compressed fluid is disclosed in WO 97/14407 to Johnston, which is incorporated herein by reference and made a part hereof. The method includes the steps of dissolving a water-insoluble drug in a solvent to form a solution. The solution is then sprayed into a compressed fluid, which can be a gas, liquid or supercritical fluid. The addition of the compressed fluid to a solution of a solute in a solvent causes the solute to attain or approach supersaturated state and to precipitate out as fine particles. In this case, the compressed fluid acts as an antisolvent which lowers the cohesive energy density of the solvent in which the drug is dissolved.

Alternatively, the drug can be dissolved in the compressed fluid which is then sprayed into an aqueous phase. The rapid expansion of the compressed fluid reduces the solvent power of the fluid, which in turn causes the solute to precipitate out as small particles in the aqueous phase. In this case, the compressed fluid acts as a solvent.

In order to stabilize the particles against aggregation, a surface modifier, such as a surfactant, is included in this technique.

Spraying into Cryogenic Fluids.

A suitable technique for precipitating by compressed fluid is disclosed by Williams et al. in U.S. Patent Pub. No. 2004/0022861, which is incorporated herein by reference and made a part hereof. The method provides a system and method for the production of small particles wherein the active ingredient is mixed with water, one or more solvents, or a combination thereof, and the resulting mixture sprayed at or below the surface of a cryogenic fluid. Frozen particles are thereby provided. Materials for encapsulating the solid particles may also be added so that frozen particles are generated wherein the encapsulating agent surrounds the active agent.

Protein Nanosphere/Microsphere Precipitation.

Particles utilized in this invention can also be produced from a process involving mixing or dissolving macromolecules such as proteins with a water soluble polymer. This process is disclosed in U.S. Pat. Nos. 5,849,884, 5,981,719, 6,090,925, 6,268,053, 6,458,387, and U.S. Patent Pub. No. 2004/0043077, which are incorporated herein by reference and made a part hereof. In an embodiment of the invention, particles are prepared by mixing a macromolecule in solution with a polymer or a mixture of polymers in solution at a pH near the isoelectric point of the macromolecule. The mixture is incubated in the presence of an energy source, such as heat, radiation, or ionization, for a predetermined amount of time. The resulting particles can be removed from any unincorporated components present in the solution by physical separation methods. There are numerous other suitable methodologies for preparing small particle dispersions capable of use in accordance with the invention.

III. Additional Methods for Preparing Particle Dispersions of Pharmaceutical Compositions The following additional processes for preparing particles of pharmaceutical compositions (i.e. active agent or organic compound) used in the present invention can be separated into four general categories. Each of the categories of processes share the steps of: (1) dissolving an organic compound in a water miscible first solvent to create a first solution, (2) mixing the first solution with a second solvent of water to precipitate the organic compound to create a pre-suspension, and (3) adding energy to the presuspension in the form of high-shear mixing or heat, or a combination of both, to provide a stable form of the organic compound having desired size ranges defined above. The mixing steps and the adding energy step can be carried out in consecutive steps or simultaneously.

The categories of processes are distinguished based upon the physical properties of the organic compound as determined through x-ray diffraction studies, differential scanning calorimetry (DSC) studies, or other suitable study conducted prior to the energy-addition step and after the energy-addition step. In the first process category, prior to the energy-addition step the organic compound in the presuspension takes an amorphous form, a semi-crystalline form or a supercooled liquid form and has an average effective particle size. After the energy-addition step the organic compound is in a crystalline form having an average effective particle size essentially the same or less than that of the presuspension.

In the second process category, prior to the energy-addition step the organic compound is in a crystalline form and has an average effective particle size. After the energy-addition step, the organic compound is in a crystalline form having essentially the same average effective particle size as prior to the energy-addition step but the crystals after the energy-addition step are less likely to aggregate or form large crystals.

The lower tendency of the organic compound to aggregate or form large crystals is observed by laser dynamic light scattering and light microscopy.

In the third process category, prior to the energy-addition step the organic compound is in a crystalline form that is friable and has an average effective particle size. What is meant by the term "friable" is that the particles are fragile and are more easily broken down into smaller particles. After the energy-addition step the organic compound is in a crystalline form having an average effective particle size smaller than the crystals of the pre-suspension. By taking the steps necessary to place the organic compound in a crystalline form that is friable, the subsequent energy-addition step can be carried out more quickly and efficiently when compared to an organic compound in a less friable crystalline morphology.

In the fourth process category, the first solution and second solvent are simultaneously subjected to the energy-addition step. Thus, the physical properties of the organic compound before and after the energy addition step were not measured.

The energy-addition step can be carried out in any fashion wherein the presuspension or the first solution and second solvent are exposed to cavitation, shearing or impact forces. In one form, the energy-addition step is an annealing step. Annealing is defined in this invention as the process of converting matter that is thermodynamically unstable into a more stable form by single or repeated application of energy (direct heat or mechanical stress), followed by thermal relaxation. This lowering of energy may be achieved by conversion of the solid form from a less ordered to a more ordered lattice structure. Alternatively, this stabilization may occur by a reordering of the surfactant molecules at the solid-liquid interface.

These four process categories are shown separately below. It should be understood, however, that the process conditions such as choice of surfactants or combination of surfactants, amount of surfactant used, temperature of reaction, rate of mixing of solutions, rate of precipitation and the like can be selected to allow for any drug to be processed under any one of the categories discussed next.

The first process category, as well as the second, third, and fourth process categories, can be further divided into two subcategories, Method A and B.

The first solvent according to the following processes is a solvent or mixture of solvents in which the organic compound of interest is relatively soluble and which is miscible with the second solvent. Such solvents include, but are not limited to water-miscible protic compounds, in which a hydrogen atom in the molecule is bound to an electronegative atom such as oxygen, nitrogen, or other Group VA, VIA and VII A in the Periodic Table of elements. Examples of such solvents include, but are not limited to, alcohols, amines (primary or secondary), oximes, hydroxamic acids, carboxylic acids, sulfonic acids, phosphonic acids, phosphoric acids, amides and ureas.

Other examples of the first solvent also include aprotic organic solvents. Some of these aprotic solvents can form hydrogen bonds with water, but can only act as proton acceptors because they lack effective proton donating groups. One class of aprotic solvents is a dipolar aprotic solvent, as defined by the International Union of Pure and Applied Chemistry (IUPAC Compendium of Chemical Terminology, 2nd Ed., 1997):

A solvent with a comparatively high relative permittivity (or dielectric constant), greater than ca. 15, and a sizable permanent dipole moment, that cannot donate suitably labile hydrogen atoms to form strong hydrogen bonds, e.g. dimethyl sulfoxide.

Dipolar aprotic solvents can be selected from the group consisting of: amides (fully substituted, with nitrogen lacking attached hydrogen atoms), ureas (fully substituted, with no hydrogen atoms attached to nitrogen), ethers, cyclic ethers, nitriles, ketones, sulfones, sulfoxides, fully substituted phosphates, phosphonate esters, phosphoramides, nitro compounds, and the like. Dimethylsulfoxide (DMSO), N-methyl-2-pyrrolidinone (NMP), 2-pyrrolidinone, 1,3-dimethylimidazolidinone (DMI), dimethylacetamide (DMA), dimethylformamide (DMF), dioxane, acetone, tetrahydrofuran (THF), tetramethylenesulfone (sulfolane), acetonitrile, and hexamethylphosphoramide (HMPA), nitromethane, among others, are members of this class.

Solvents may also be chosen that are generally water-immiscible, but have sufficient water solubility at low volumes (less than 10%) to act as a water-miscible first solvent at these reduced volumes. Examples include aromatic hydrocarbons, alkenes, alkanes, and halogenated aromatics, halogenated alkenes and halogenated alkanes. Aromatics include, but are not limited to, benzene (substituted or unsubstituted), and monocyclic or polycyclic arenes. Examples of substituted benzenes include, but are not limited to, xylenes (ortho, meta, or para), and toluene. Examples of alkanes include but are not limited to hexane, neopentane, heptane, isooctane, and cyclohexane. Examples of halogenated aromatics include, but are not restricted to, chlorobenzene, bromobenzene, and chlorotoluene. Examples of halogenated alkanes and alkenes include, but are not restricted to, trichloroethane, methylene chloride, ethylenedichloride (EDC), and the like.

Other specific examples of solvents suitable for use as the first solvent include, but are not limited to: N-methyl-2-pyrrolidinone (also called N-methyl-2-pyrrolidone), 2-pyrrolidinone (also called 2-pyrrolidone), 1,3-dimethyl-2-imidazolidinone (DMI), dimethylsulfoxide, dimethylacetamide, acetic acid, lactic acid, methanol, ethanol, isopropanol, 3-pentanol, n-propanol, benzyl alcohol, glycerol, butylene glycol (butanediol), ethylene glycol, propylene glycol, monoacylated and diacylated monoglycerides (such as glyceryl caprylate), dimethyl isosorbide, acetone, dimethylsulfone, dimethylformamide, 1,4-dioxane, tetramethylenesulfone (sulfolane), acetonitrile, nitromethane, tetramethylurea, hexamethylphosphoramide (HMPA), tetrahydrofuran (THF), dioxane, diethylether, tert-butylmethyl ether (TBME), aromatic hydrocarbons, alkenes, alkanes, halogenated aromatics, halogenated alkenes, halogenated alkanes, xylene, toluene, benzene, substituted benzene, ethyl acetate, methyl acetate, butyl acetate, chlorobenzene, bromobenzene, chlorotoluene, trichloroethane, methylene chloride, ethylenedichloride (EDC), hexane, neopentane, heptane, isooctane, cyclohexane, polyethylene glycol (PEG, for example, PEG-4, PEG-8, PEG-9, PEG-12, PEG-14, PEG-16, PEG-120, PEG-75, PEG-150), polyethylene glycol esters (examples such as PEG-4 dilaurate, PEG-20 dilaurate, PEG-6 isostearate, PEG-8 palmitostearate, PEG-150 palmitostearate), polyethylene glycol sorbitans (such as PEG-20 sorbitan isostearate), polyethylene glycol monoalkyl ethers (examples such as PEG-3 dimethyl ether, PEG-4 dimethyl ether), polypropylene glycol (PPG), polypropylene alginate, PPG-10 butanediol, PPG-10 methyl glucose ether, PPG-20 methyl glucose ether, PPG-15 stearyl ether, propylene glycol dicaprylate/dicaprate, propylene glycol laurate, and glycofurol (tetrahydrofurfuryl alcohol polyethylene glycol ether). A preferred first solvent is N-methyl-2-pyrrolidinone. Another preferred first solvent is lactic acid.

The second solvent is an aqueous solvent. This aqueous solvent may be water by itself. This solvent may also contain buffers, salts, surfactant(s), water-soluble polymers, and combinations of these excipients.

Method A.

In Method A, the organic compound ("active agent" or "drug") is first dissolved in the first solvent to create a first solution. The organic compound can be added from about 0.1% (w/v) to about 50% (w/v) depending on the solubility of the organic compound in the first solvent. Heating of the concentrate from about 30° C. to about 100° C. may be necessary to ensure total dissolution of the compound in the first solvent.

A second aqueous solvent is provided with one or more optional surface modifiers such as an anionic surfactant, a cationic surfactant, a zwitterionic surfactant, a nonionic surfactant or a biologically surface active molecule added thereto. Suitable anionic surfactants include but are not limited to alkyl sulfonates, alkyl phosphates, alkyl phosphonates, potassium laurate, triethanolamine stearate, sodium lauryl sulfate, sodium dodecylsulfate, alkyl polyoxyethylene sulfates, sodium alginate, dioctyl sodium sulfosuccinate, phosphatidyl glycerol, phosphatidyl inosine, phosphatidylinositol, diphosphatidylglycerol, phosphatidylserine, phosphatidic acid and their salts, sodium carboxymethylcellulose, cholic acid and other bile acids (e.g., cholic acid, deoxycholic acid, glycocholic acid, taurocholic acid, glycodeoxycholic acid) and salts thereof (e.g., sodium deoxycholate, etc.).

Zwitterionic surfactants are electrically neutral but possess local positive and negative charges within the same molecule. Suitable zwitterionic surfactants include but are not limited to zwitterionic phospholipids. Suitable phospholipids include phosphatidylcholine, phosphatidylethanolamine, diacyl-glycero-phosphoethanolamine (such as dimyristoyl-glycero-phosphoethanolamine (DMPE), dipalmitoyl-glycero-phosphoethanolamine (DPPE), distearoyl-glycero-phosphoethanolamine (DSPE), and dioleolyl-glycero-phosphoethanolamine (DOPE)). Mixtures of phospholipids that include anionic and zwitterionic phospholipids may be employed in this invention. Such mixtures include but are not limited to lysophospholipids, egg or soybean phospholipid or any combination thereof. The phospholipid, whether anionic, zwitterionic or a mixture of phospholipids, may be salted or desalted, hydrogenated or partially hydrogenated, or natural, semisynthetic, or synthetic. The phospholipid may also be conjugated with a water-soluble or hydrophilic polymer to specifically target the delivery to macrophages in the present invention. However, conjugated phospholipids may be used to target other cells or tissue in other applications. A preferred polymer is polyethylene glycol (PEG), which is also known as the monomethoxy polyethyleneglycol (mPEG). The molecule weights of the PEG can vary, for example, from 200 to 50,000. Some commonly used PEG's that are commercially available include PEG 350, PEG 550, PEG 750, PEG 1000, PEG 2000, PEG 3000, and PEG 5000. The phospholipid or the PEG-phospholipid conjugate may also incorporate a functional group which can covalently attach to a ligand including but not limited to proteins, peptides, carbohydrates, glycoproteins, antibodies, or pharmaceutically active agents. These functional groups may conjugate with the ligands through, for example, amide bond formation, disulfide or thioether formation, or biotin/streptavidin binding. Examples of the ligand-binding functional groups include but are not limited to hexanoylamine, dodecanylamine, 1,12-dodecanedicarboxylate, thioethanol, 4-(p-maleimidophenyl)butyramide (MPB), 4-(p-maleimidomethyl)cyclohexane-carboxamide (MCC), 3-(2-pyridyldithio)propionate (PDP), succinate, glutarate, dodecanoate, and biotin.

Suitable cationic surfactants include but are not limited to quaternary ammonium compounds, such as benzalkonium chloride, cetyltrimethylammonium bromide, chitosans, lauryldimethylbenzylammonium chloride, acyl camitine hydrochlorides, dimethyldioctadecylammomium bromide (DDAB), dioleyoltrimethylammonium propane (DOTAP), dimyristoyltrimethylammonium propane (DMTAP), dimethylaminoethanecarbamoyl cholesterol (DC-Chol), 1,2-diacylglycero-3-(O-alkyl)phosphocholine, O-alkylphosphatidylcholine, alkyl pyridinium halides, or long-chain alkyl amines such as, for example, n-octylamine and oleylamine.

Suitable nonionic surfactants include: glyceryl esters, polyoxyethylene fatty alcohol ethers (MACROGOL™ and BRIJ™), polyoxyethylene sorbitan fatty acid esters (polysorbates), polyoxyethylene fatty acid esters (MYRJ™), sorbitan esters (SPAN™), glycerol monostearate, polyethylene glycols, polypropylene glycols, cetyl alcohol, cetostearyl alcohol, stearyl alcohol, aryl alkyl polyether alcohols, polyoxyethylene-polyoxypropylene copolymers (poloxamers), poloxamines, methylcellulose, hydroxymethylcellulose, hydroxypropylcellulose, hydroxypropylmethylcellulose, noncrystalline cellulose, polysaccharides including starch and starch derivatives such as hydroxyethylstarch (HES), polyvinyl alcohol, and polyvinylpyrrolidone. In a preferred form, the nonionic surfactant is a polyoxyethylene and polyoxypropylene copolymer and preferably a block copolymer of propylene glycol and ethylene glycol. Such polymers are sold under the trade name POLOXAMER also sometimes referred to as PLURONIC®, and sold by several suppliers including Spectrim Chemical and Ruger. Among polyoxyethylene fatty acid esters is included those having short alkyl chains. One example of such a surfactant is SOLUTOL® HS15, polyethylene-660-hydroxystearate, manufactured by BASF Aktiengesellschaft.

Surface-active biological molecules include such molecules as albumin, casein, hirudin or other appropriate proteins. For example, proteins having hydrophilic and hydrophobic domains also can be used. Polysaccharide surface active biologics are also included, and consist of but are not limited to, starches, heparins, and chitosans. Other suitable surfactants include any amino acids such as leucine, alanine, valine, isoleucine, lysine, aspartic acid, glutamic acid, methionine, phenylalanine, or any derivatives of these amino acids such as, for example, amide or ester derivatives and polypeptides formed from these amino acids.

It may also be desirable to add a pH adjusting agent to the second solvent. Suitable pH adjusting agents include, but are not limited to, hydrochloric acid, sulfuric acid, phosphoric acid, monocarboxylic acids (such as, for example, acetic acid and lactic acid), dicarboxylic acids (such as, for example, succinic acid), tricarboxylic acids (such as, for example, citric acid), THAM (tris(hydroxymethyl)aminomethane), meglumine (N-methylglucosamine), sodium hydroxide, and amino acids such as glycine, arginine, lysine, alanine, histidine and leucine. The second solvent should have a pH within the range of from about 3 to about 11. The aqueous medium may additionally include an osmotic pressure adjusting agent, such as but not limited to glycerin, a monosaccharide such as dextrose, a disaccharide such as sucrose, a trisaccharide such as raffinose, and sugar alcohols such as mannitol, xylitol and sorbitol.

For oral dosage forms, one or more of the following excipients may be utilized: gelatin, casein, lecithin (phosphatides), gum acacia, cholesterol, tragacanth, stearic acid, benzalkonium chloride, calcium stearate, glyceryl monostearate, cetostearyl alcohol, cetomacrogol emulsifying wax, sorbitan esters, polyoxyethylene alkyl ethers, e.g., macrogol ethers such as cetomacrogol 1000, polyoxyethylene castor oil derivatives, polyoxyethylene sorbitan fatty acid esters, e.g., the commercially available TWEENS™, polyethylene glycols, polyoxyethylene stearates, colloidal silicon dioxide, phosphates, sodium dodecylsulfate, carboxymethylcellulose calcium, carboxymethylcellulose sodium, methylcellulose, hydroxyethylcellulose, hydroxypropylcellulose, hydroxypropylmethylcellulose phthalate, noncrystalline cellulose, magnesium aluminum silicate, triethanolamine, polyvinyl alcohol (PVA), and polyvinylpyrrolidone (PVP). Most of these excipients are described in detail in the Handbook of Pharmaceutical Excipients, published jointly by the American Pharmaceutical Association and The Pharmaceutical Society of Great Britain, the Pharmaceutical Press, 1986. The surface modifiers are commercially available and/or can be prepared by techniques known in the art. Two or more surface modifiers can be used in combination.

In a preferred form, the method for preparing small particles of an organic compound includes the steps of adding the first solution to the second solvent. The addition rate is dependent on the batch size, and precipitation kinetics for the organic compound. Typically, for a small-scale laboratory process (preparation of 1 liter), the addition rate is from about 0.05 cc per minute to about 10 cc per minute. During the addition, the solutions should be under constant agitation. It has been observed using light microscopy that amorphous particles, semi-crystalline solids, or a supercooled liquid are formed to create a pre-suspension. The method further includes the step of subjecting the pre-suspension to an energy-addition step to convert the amorphous particles, supercooled liquid or semicrystalline solid to a more stable, crystalline solid state. The resulting particles will have an average effective particles size as measured by dynamic light scattering methods (e.g., photocorrelation spectroscopy, laser diffraction, low-angle laser light scattering (LALLS), medium-angle laser light scattering (MALLS), light obscuration methods (Coulter method, for example), rheology, or microscopy (light or electron) within the ranges set forth above). In process category four, the first solution and the second solvent are combined while simultaneously conducting the energy-addition step.

The energy-addition step involves adding energy through sonication, homogenization, countercurrent flow homogenization, microfluidization, or other methods of providing impact, shear or cavitation forces. The sample may be cooled or heated during this stage. In one form, the energy-addition step is effected by a piston gap homogenizer such as the one sold by Avestin Inc. under the product designation EmulsiFlex-C160. In another form, the energy-addition step is accomplished by ultrasonication using an ultrasonic processor such as the Vibra-Cell Ultrasonic Processor (600 W), manufactured by Sonics and Materials, Inc. In yet another form, the energy-addition step is accomplished by use of an emulsification apparatus as described in U.S. Pat. No. 5,720,551, which is incorporated herein by reference and made a part hereof.

Depending upon the rate of energy addition, it may be desirable to adjust the temperature of the processed sample to within the range of from approximately −30° C. to 30° C. Alternatively, in order to effect a desired phase change in the processed solid, it may also be necessary to heat the pre-suspension to a temperature within the range of from about 30° C. to about 100° C. during the energy-addition step.

Method B.

Method B differs from Method A in the following respects. The first difference is a surfactant or combination of surfactants is added to the first solution. The surfactants may be selected from the groups of anionic, nonionic, cationic surfactants, and surface-active biological modifiers set forth above.

Comparative Example of Method A and Method B and U.S. Pat. No. 5,780,062.

U.S. Pat. No. 5,780,062 discloses a process for preparing small particles of an organic compound by first dissolving the compound in a suitable water-miscible first solvent. A second solution is prepared by dissolving a polymer and an amphiphile in aqueous solvent. The first solution is then added to the second solution to form a precipitate that consists of the organic compound and a polymer-amphiphile complex. The '062 patent does not disclose utilizing the energy-addition step of this process in Methods A and B. Lack of stability is typically evidenced by rapid aggregation and particle growth. In some instances, amorphous particles recrystallize as large crystals. Adding energy to the pre-suspension in the manner disclosed above typically affords particles that show decreased rates of particle aggregation and growth, as well as the absence of recrystallization upon product storage.

Methods A and B are further distinguished from the process of the '062 patent by the absence of a step of forming a polymer-amphiphile complex prior to precipitation. In Method A, such a complex cannot be formed as no polymer is added to the diluent (aqueous) phase. In Method B, the surfactant, which may also act as an amphiphile, or polymer, is dissolved with the organic compound in the first solvent. This precludes the formation of any amphiphile-polymer complexes prior to precipitation. In the '062 patent, successful precipitation of small particles relies upon the formation of an amphiphile-polymer complex prior to precipitation. The '062 patent discloses the amphiphile-polymer complex forms aggregates in the aqueous second solution. The '062 patent explains the hydrophobic organic compound interacts with the amphiphile-polymer complex, thereby reducing solubility of these aggregates and causing precipitation. In the present process, it has been demonstrated that the inclusion of the surfactant or polymer in the first solvent (Method B) leads, upon subsequent addition to second solvent, to formation of a more uniform, finer particulate than is afforded by the process outlined by the '062 patent.

Coating of the Particles

The processes for coating the particles prepared by the present invention can be accomplished through various techniques known to those skilled in the art. The coating can be associated with the particle through various associations, including covalent and/or non-covalent associations (e.g., covalent bonding, ionic interactions, electrostatic interactions, dipole-dipole interactions, hydrogen bonding, van der Waal's forces, hydrophobic/hydrophobic domain interactions, cross-linking, and/or any other interactions).

Non-covalently bound coatings can be prepared, for example, by mixing a plurality of particles with a solution comprising an opsonin such as immunoglobulin G (IgG) or a complement protein such as C3b or C5. The solution can be mixed under high-shear conditions using, for example, a microfluidizer, a piston gap homogenizer, a counter-current flow homogenizer, or an ultrasonic processor. To confirm the coating successfully adsorbs to the particles, the surface electrical potential of the particles can be determined by measuring the zeta potential before and after the coating process. Other known methods for measuring the adsorption of coatings also can be used, for example, the opsonin can be modified with a fluorescent label and absorption of the fluorescently-labeled opsonin can be detected by fluorescence microscopy. ELISA methods or other antibody-based detection systems also can be used to detect the opsonin. Advantageously, the opsonin coatings can easily adsorb to the surface of particles, particularly particles comprising poorly water soluble active agents, as explained above.

The coating also can be covalently associated with the particle core. Covalently bound coatings can be prepared for example, by mixing a plurality of particles, said particles comprising a reactive functional group with a solution comprising an opsonin. Reactive functional groups include electrophilic functional groups capable of reacting, for example, with the amino-, hydroxyl-, and/or thiol-containing amino acids of the opsonin. Suitable reactive functional groups include, for example, aldehydes, N-hydroxy-succinimide esters, and maleimides. Unstable covalent bonds formed by the foregoing reactions can be stabilized by further reaction steps. For example, reaction of an amine with an aldehyde forms a hydrolytically unstable imine that can be stabilized by reduction of the imine bond using a reducing agent such as sodium borohydride or sodium cyanoborohydride.

In yet another aspect, the coating can comprise an opsonin that is covalently bound to another molecule of the coating, such as a polysaccharide. Typically, the particle comprising an active agent is first coated with a polysaccharide and then the polysaccharide is reacted with the opsonin, for example, using the covalent bond methods described immediately above. The polysaccharide or other suitable molecule conjugated to the opsonin can be used to modify the properties of the coating, for example, by improving the binding affinity of the coating to the particle core. Suitable polysaccharides include, but are not limited to dextrans, glucans, celluloses, starches, glycogens, fructans, chitins, and heparins. The polysaccharides generally have a molecular weight of between about 5,000 daltons and about 250,000 daltons, for example, between about 8,000 daltons and about 200,000 daltons, and/or between about 10,000 daltons and about 150,000 daltons, but higher and lower molecular weight polysaccharides also can be used.

The coating can further include a single surfactant, or a combination of surfactants. The surfactant can be selected from a variety of known anionic surfactants, cationic surfactants, zwitterionic surfactants, nonionic surfactants and surface active biological modifiers. Suitable surfactants include the surfactants previously set forth herein. Exemplary surfactants include, but are not limited to, poloxamers, phospholipids, polyethylene glycol-conjugated phospholipids, and polysorbates. Exemplary combinations of surfactants include, but are not limited to, poloxamers and phospholipids, poloxamers and polyethylene glycol-conjugated phospholipids, and poloxamers and polysorbates. Alternatively, the coating can be substantially free of surfactant (e.g., less than 2 weight percent of surfactant, less than 1 weight percent of surfactant, or less than 0.5 weight percent of surfactant).

Cellular Uptake of Coated Particles

One embodiment of the present invention is directed to a method of enhancing cellular uptake of an active agent, comprising contacting cells with a plurality of surface-modified particles, said particles comprising a particle core and a coating associated with the particle core. The cells can be phagocytic cells, weakly phagocytic cells, or non-phagocytic cells. The particle core comprises an active agent, the coating comprises an opsonin (e.g., an antibody having an isotype of IgG or a complement protein such as C3b or C5), and the surface-modified particle has an average size from about 1 nm to about 2,000 nm. Uptake of the active agent by the cells is thereby enhanced, relative to the uptake of active agent when particles that do not comprise the aforementioned coating are used.

Uptake by cells allows the active agent to be delivered to target tissues in need of treatment because the various cell types capable of enhanced uptake of the coated particles in accordance with the disclosure also traffic to diseased or inflamed tissues. For example, neutrophils predominate early in infection or inflammation, followed by monocyte-derived phagocytes that leave the blood vasculature and enter infected tissue. Fixed macrophages (histiocytes) abound in the liver, nervous system, lungs, lymph nodes, bone marrow, and several other tissues. Tissues that are most affected by bacterial, viral or fungal pathogens and which are inflamed can be targeted by delivery of drug-loaded cells (granulocytes, for example) having a propensity to be directed to these inflammation sites by chemotaxis. Thus, by promoting uptake by cells, the pharmaceutical agent is released from these cells in a the region where it is therapeutically most needed. Thus, delivery of the agent to a target tissue for treatment of a disease or disorder is facilitated by the cells loaded with coated particles. Such diseases and disorders include, but are not limited to, infectious diseases or disorders, inflammatory diseases or disorders, neurodegenerative diseases or disorders, and proliferative diseases or disorders.

There are numerous phagocytic cell types that are capable of uptake of coated particles. These cells include, but are not limited to, macrophages, monocytes, granulocytes, agranulocytes and neutrophils. The present invention also encompasses weakly phagocytic cells and non-phagocytic cells. Thus, other suitable cell types include, but are not limited to, T-lymphocytes, B-lymphocytes, null cells, natural killer cells, lymphocytes, red blood cells, muscle cells, bone marrow cells, stem cells, bone cells, vascular cells, organ tissue cells, neuronal cells, basophils, eosinophils, dendritic cells, and endothelial cells. Still other cells can be used to deliver the pharmaceutically active compounds to a subject. Any cell type may be used in the present invention so long as it is capable of uptake of the particle. Uptake by the cells of the particles may include phagocytosis, or other means of endocytosis, or attachment/adsorption of the particle onto the surface of the cells. Particles associated with the cell surface can also be taken into the cells by pinocytosis, which is an invagination of the cell membrane to form an intracellular capsule around the particle. In pinocytosis ("cell drinking"), the engulfed particle is relatively small (e.g., 20 nm) (Watts et al., Endocytosis: what goes in and how?, Journal of Cell Science, 1992, volume 103(1), pages 1-8). Pinocytosis occurs continuously in almost all eucaryotic cells.

As explained herein, the particles advantageously include a coating which facilitates cellular uptake. In particular, the coating can facilitate uptake by cells such as monocytes, macrophages, and T-lymphocytes, which are capable of trafficking by known mechanisms such as chemotaxis to a site of inflammation, infection, and/or tumor and thereby deliver the particles to a particular target tissue.

In one aspect of the invention, the contacting of the cells to the surface-modified particle (to form cells loaded with the active agent) is carried out ex vivo (i.e., outside of a mammalian subject). Alternatively, or in addition, the contacting of the cells to the surface-modified particle can be carried out in vivo (i.e., inside a mammalian subject). An amount of the surface modified particle that is effective to treat a disease or disorder is used during the contacting step. One of ordinary skill understands that a certain amount of the particles may be taken up by a cell type that does not traffic to a target tissue of interest, or is not released by the cell at the target tissue of interest. Therefore, one of ordinary skill understands that the amounts of particles administered may be optimized by routine protocols, provided that such amounts are within established administration protocols.

For ex-vivo administration, the cells can be isolated from a mammalian subject using a cell separator or apheresis device. For instance, the CS-3000™ cell separator (Fenwal Inc., Lake Zurich, Ill.) or the ISOLEX™ cell separator (Baxter Healthcare Corp., Deerfield, Ill.) can be used to isolate various cells. Other methods known to those skilled in the art of ex-vivo cell isolation can be employed to obtain cells useful in the present invention. Such methods include, but are not limited to, apheresis of peripheral blood, mobilization of bone marrow cells through, e.g., G-CSF, M-CSF, or GM-CSF, or direct removal of marrow cells by spinal, sternal, lumbar, or iliac crest puncture. The ex-vivo cells can be maintained in a cell culture medium or other isolating system known to those skilled in the art. Examples of such media are Alserver's Solution, Ames' Medium, Eagle's Basal Medium, CHO (Chinese Hamster Ovary) cell culture media, Click's Medium, Dulbecco's Modified Eagle's Medium, phosphate-buffered saline, phosphate-buffered dextrose or sucrose, Earle's Balanced Salt Solution, Gene Therapy Medium-3, Gey's Balanced Salt Solution, Glasgow Minimum Essential Medium, Hanks' Balanced Salt Solutions, Hybridoma Media, Iscove's Modified Dulbecco's Medium, Krebs-Henseleit Buffer with sugars, Leibovitz Media (L-15), M16 Medium, McCoy's Medium, MCDB, MDBK (Madin-Darby Bovine Kidney), MDCK (Madin-Darby Canine Kidney), Medium 199, NCTC, Ham's Media (e.g., Nutrient Mixture F-10), Coon's Modified Ham's Medium, RPMI, and others such as those listed in Biochemicals & Reagents for Life Science Research, Sigma-Aldrich Co. (St. Louis, Mo., USA). The purpose of the culture so described may be for the purpose of simple storage without loss of cells, or for cell proliferation or expansion, by appropriate addition of growth factors, cytokines, and nutrients, to encourage cell expansion. Such expansion would minimize the number of times that a patient would have to be prepared for removal of cellular samples.

Once isolated, the cells can be contacted with the coated particles and incubated for a short period of time to allow for cell uptake of the particles. The concentrations of particles used in the ex-vivo procedure will vary due to several factors, including, but not limited to, type of cells used, concentration of cells, active agent employed, size of the small particle dispersions, disease to be treated, and so on. Generally, however, the cellular isolates are contacted with about 1 to about 300 mg/ml of particles of the present invention. During contact of the particles with the cells, the particles are at a concentration higher than the thermodynamic saturation solubility, thereby allowing the particles to remain in particulate form during uptake and delivery to the mammalian subject. The cells can be incubated with the particles for up to 24 hours or longer to permit sufficient cell uptake of the drug particles.

Any method to effect uptake of particles of active agent by ex vivo cells can be used with the requirement that the method does not destroy or otherwise make the cells non-useful for administration to a subject. For example, site-specific delivery of the particle via a biorecognition molecule may be used. See, e.g., U.S. Patent Publication No. 2003/0092069, incorporated herein by reference, which discloses the transferring of genes into specific cells or tissues via a hollow nanoparticle. Other methods of loading the ex-vivo cells include electroporation, sonoporation, and other mechanical means that disrupt the cell membrane (sonication, for example) and enable insertion of solid particulates into the cells. Ultrasound was successfully used by Zarnitsyn et al. (Zarnitsyn et al., Physical parameters influencing optimization of ultrasound-mediated DNA transfection, Ultrasound Med. Biol., 2004, volume 30(4), pages 527-538) to transiently disrupt cell membranes and thereby facilitate the loading of DNA into viable cells. Other mechanical procedures are well-known to those experienced in the art, and are included as part of this disclosure. Chemical methods of transiently destabilizing cell membranes are also well known. Transfection reagents contain surface active agents and include 293F CTIN™ Transfection Reagent and LIPOFECTAMINE™, both products of Invitrogen Corporation (Carlsbad, Calif.). Another example of a surfactant used to transfer DNA into cells is the SAINT™ reagent from Synvolux Therapeutics B. V. L. J. (Groningen, The Netherlands), which is based on a pyridinium surfactant.

The following description of particles also applies to all embodiments disclosed herein. For marginally soluble drugs, the cell loading procedure can be utilized provided that the cells are able to take up the coated active agent particles at a faster rate than the competing dissolution process. The particles should be of an appropriate size to allow for the cells to take up the coated particles and deliver them to the target tissue before complete dissolution of the particle. Because cells which are known to traffic to the target tissue of interest are capable of taking up the particles, the active agent is ultimately released from the cells in the vicinity of the target tissue. Furthermore, the concentration of the active agent composition should be kept higher than the saturation solubility of the composition so that the particle is able to remain in the crystalline state during uptake.

The following description of particles also applies to all embodiments disclosed herein. Administering of the surface-modified particle can be performed by various techniques known in the art for administering particles. Administering includes administering the surface-modified particle to a mammalian subject. Suitable methods for administering of the surface-modified particle include, but are not limited to, administering the particle intravenously, intraarterially, intramuscularly, subcutaneously, intradermally, intraarticularly, intrathecally, epidurally, intracerebrally, buccally, rectally, topically, transdermally, orally, intranasally, via the pulmonary route, intraperitoneally, and/or intraophthalmically. The step of administering can be by bolus injection, by intermittent infusion, or by continuous infusion. The amount of surface-modified particle and method of delivery can be determined by skilled clinicians. Various factors will affect the amount and method of delivery including, but not limited to, the type of cells used (for ex vivo methods of administration), the sex, weight and age of the subject to be treated, the type and maturity of the disease or disorder to be treated, the active agent to be administered, and so on. Generally, the active agent can be provided in doses ranging from 1 pg compound/kg body weight to 1000 mg/kg, 0.1 mg/kg to 100 mg/kg, 0.1 mg/kg to 50 mg/kg, and 1 to 20 mg/kg, given in daily doses or in equivalent doses at longer or shorter intervals, e.g., every other day, twice weekly, weekly, or twice or three times daily.

Various diseases or disorders can be treated by the present methods including, but not limited to, infectious diseases or disorders, inflammatory diseases or disorders, neurodegenerative diseases or disorders, and proliferative diseases or disorders. In this regard, symptoms of such diseases or disorders can be alleviated by the present methods.

"Infectious diseases or disorder" as used herein refers to a condition caused by pathogenic microorganisms, such as bacteria, viruses, parasites or fungi. Infectious diseases or disorders that can benefit from the disclosed methods include, but are not limited to, viral infections (including retroviral infections) such as dengue, enterovirus infections, HIV, hepatitis B, hepatitis C, and influenza; fungal infections; parasitic infections such as African trypanosomiasis and malaria; and bacterial infections such as cholera, meningitis, and tuberculosis.

"Inflammatory disease or disorder" as used herein refers to a condition characterized by redness, heat, swelling, and pain (i.e., inflammation) that typically involves tissue injury or destruction. Inflammatory diseases or disorders are notably associated with the influx of leukocytes and/or leukocyte chemotaxis. Inflammatory conditions may result from infection with pathogenic organisms or viruses and from noninfectious events including but not limited to trauma or reperfusion following myocardial infarction or stroke, immune responses to foreign antigens, and autoimmune responses. Accordingly, inflammatory conditions amenable to treatment with the methods and compounds of the invention encompass conditions associated with reactions of the specific defense system, conditions associated with reactions of the non-specific defense system, and conditions associated with inflammatory cell activation.

As used herein, the term "specific defense system" refers to the component of the immune system that reacts to the presence of specific antigens. Examples of inflammatory conditions resulting from a response of the specific defense system include but are not limited to the classical response to foreign antigens, autoimmune diseases, and delayed type hypersensitivity response mediated by B-cells and/or T-cells (i.e., B-lymphocytes and/or T-lymphocytes). Chronic inflammatory diseases, the rejection of solid transplanted tissue and organs including but not limited to kidney and bone marrow transplants, and graft versus host disease (GVHD), are further examples of inflammatory conditions resulting from a response of the specific defense system.

The term "non-specific defense system" as used herein refers to inflammatory conditions that are mediated by leukocytes that are incapable of immunological memory (e.g., granulocytes including but not limited to neutrophils, eosinophils, and basophils, mast cells, monocytes, macrophages). Examples of inflammatory conditions that result, at least in part, from a reaction of the non-specific defense system include but are not limited to adult (acute) respiratory distress syndrome (ARDS), multiple organ injury syndromes, reperfusion injury, acute glomerulonephritis, reactive arthritis, dermatitis with acute inflammatory components, acute purulent meningitis, other central nervous system inflammatory conditions including but not limited to stroke, thermal injury, inflammatory bowel disease, granulocyte transfusion associated syndromes, and cytokine-induced toxicity.

The therapeutic methods of the invention include methods for the amelioration of conditions associated with inflammatory cell activation. "Inflammatory cell activation" refers to the induction by a stimulus (including but not limited to cytokines, antigens, and auto-antibodies) of a proliferative cellular response, the production of soluble mediators (including but not limited to cytokines, oxygen radicals, enzymes, prostanoids, and vasoactive amines), or cell surface expression of new or increased numbers of mediators (including but not limited to major histocompatability antigens and cell adhesion molecules) in inflammatory cells (including but not limited to monocytes, macrophages, T lymphocytes, B lymphocytes, granulocytes (polymorphonuclear leukocytes including neutrophils, basophils, and eosinophils), mast cells, dendritic cells, Langerhans cells, and endothelial cells). It will be appreciated by persons skilled in the art that the activation of one or a combination of these phenotypes in these cells can contribute to the initiation, perpetuation, or exacerbation of an inflammatory condition.

Other diseases or disorders which can be successfully treated include diseases or disorders characterized by inflammation or infection, including but not limited to, rheumatoid arthritis, Graves' disease, myasthenia gravis, thyroiditis, diabetes, inflammatory bowel disease, autoimmune oophoritis, systemic lupus erythematosus, and Sjögren's syndrome.

Examples of neurodegenerative diseases or disorders which can be successfully treated include, but are not limited to, Parkinson's disease, Alzheimer's disease, multiple sclerosis, encephalomyelitis, encephalitis (including HIV encephalitis), Huntington's disease, amyotrophic lateral sclerosis (also known as Lou Gehrig's disease), frontotemporal dementia, prion diseases, Creutzfeldt-Jakob disease, and adrenoleukodystrophy. Other neurodegenerative diseases or disorders which can be successfully treated include Pick's disease, frontotemporal lobar degeneration, progressive aphasia, and semantic dementia. Prion diseases, also known as transmissible spongiform encephalopathies (TSEs), include Creutzfeldt-Jakob disease, new variant Creutzfeldt-Jakob disease, Gerstmann-Straussler-Scheinker syndrome, fatal familial insomnia, and kuru. The neurodegenerative diseases or disorders also can be Alexander disease, Alper's disease, ataxia telangiectasia, Batten disease (also known as Spielmeyer-Vogt-Sjogren-Batten disease), Canavan disease, Cockayne syndrome, corticobasal degeneration, HIV-associated dementia, Kennedy's disease, Krabbe disease, Lewy body dementia, Machado-Joseph disease (spinocerebellar ataxia type 3), multiple system atrophy, neuroborreliosis, Pelizaeus-Merzbacher disease, primary lateral sclerosis, Refsum's disease, Sandhoff disease, Schilder's disease, schizophrenia, spinocerebellar ataxia, spinal muscular atrophy, Steele-Richardson-Olszewski disease, and tabes dorsalis.

Proliferative diseases or disorders that can benefit from the disclosed methods include, but are not limited to, colon cancer, kidney cancer, non small cell lung cancer, small cell lung cancer, cervical cancer, breast cancer, prostate cancer, brain cancer, sarcoma, melanoma, leukemia, acute lymphocytic leukemia, acute myelogenous leukemia, chronic lymphocytic leukemia, chronic myelogenous leukemia, Hodgkin lymphoma, non-Hodgkin lymphoma, mycloma, and glioblastoma. Thyroiditis includes Hashimoto's thyroiditis, subacute thyroiditis (also known as de Quervain's thyroiditis), silent thyroiditis (also known as painless thyroiditis), post partum thyroiditis, drug-induced thyroiditis, radiation-induced thyroiditis, and acute suppurative thyroiditis.

The disclosure may be better understood by reference to the following examples which are not intended to be limiting, but rather only set forth exemplary embodiments in accordance with the disclosure.

EXAMPLES

Example 1

Preparation of Superparamagnetic Iron Oxide (SPIO) Particles with IgG Coating

Sodium periodate, sodium cyanoborohydride, neocuproine, ammonium acetate, ascorbic acid and potassium permanganate were purchased from Sigma-Aldrich, St. Louis, Mo. Murine and human IgG F(ab')$_2$ and Fc fragments were purchased from Jackson ImmunoResearch Laboratories, Inc., West Grove, Pa. Rat IgG2a anti-MsCD16/CD32 (FcgRIII/FcgRII) (2.4G2), Rat IgG2a anti-trinitrophenol (TNP) isotype control, IgG1 anti-Hu CD16 (FcgRIII) (3G8), IgG1 anti-Hu CD32 (FcgRII) (3D3), IgG1 anti-TNP (107.3) were purchased from BD Biosciences, San Jose, Calif. IgG1 anti-Hu CD64 (FcgRI) (10.1) was purchased from eBioscience, San Diego, Calif. Alexa Fluor® 488 carboxylic acid, succinimidyl ester and Alexa Fluor® 488 hydroxylamine were purchased from Invitrogen. Ferumoxides (Feridex IV®, Bayer Healthcare Pharmaceuticals, Wayne, N.J.) is a superparamagnetic iron oxide (SPIO) particle with an average hydrodynamic size of 150 nm and concentration of iron at 11.2 mg/mL.

SPIO nanoparticles (NP) were concentrated using a Microcon YM-30 centrifugal filter unit (Millipore, Billerica, Mass.) and dialyzed against acetate buffer (0.1 M, pH 5.5) overnight at 4° C. Dextran T-10 surrounding the iron core of SPIO was oxidized by reaction with 10 mM sodium metaperiodate in the dark for 1 hour at room temperature. To remove excess reagent, oxidized SPIO were dialyzed against phosphate-buffered saline (PBS) overnight at 4° C. Human IgG (Baxter Heathcare Corporation, Westlake Village, Calif.) or murine IgG (Jackson ImmunoResearch Laboratories, Inc.) were added to the oxidized NP suspension in PBS with 50 mM of sodium cyanoborohydride in 1 M NaOH at final concentrations of 2 mg/ml IgG and 10 mg/ml SPIO. The incubation was performed overnight under gentle stirring at room temperature and the reaction was quenched by addition of 50 mM Tris-HCl. Free IgG was removed from the NP using Sepharose CL-4B column. Sepharose CL-4B chromatography of the NP conjugate reactions showed that NP eluted between 20 ml and 25 ml and the free IgG between 45 ml and 60 ml (FIG. 1).

Particle size was measured by dynamic light scattering. The presence of IgG covalently attached to NP and free IgG amount were estimated using the micro bicinchoninic acid (BCA) assay (Pierce Biotechnology, Rockford, Ill.). The coupling yield was estimated at approximately 50%.

In parallel preparations, Alexa Fluor® 488 hydroxylamine, mouse IgG and mouse and human IgG F(ab')$_2$ fragments were reacted with aldehyde SPIO at room temperature in PBS buffer to obtain control reagents for Fc blocking studies and to synthesize combined fluorescence and antibody conjugated SPIO preparations. For fluorescent nanoformulations, Alexa Fluor® 488 carboxylic acid succinimidyl ester was conjugated with IgG SPIO in carbonate-bicarbonate buffer for 2 h. The free dye was separated from conjugates using PD-10 columns.

Figure 2:
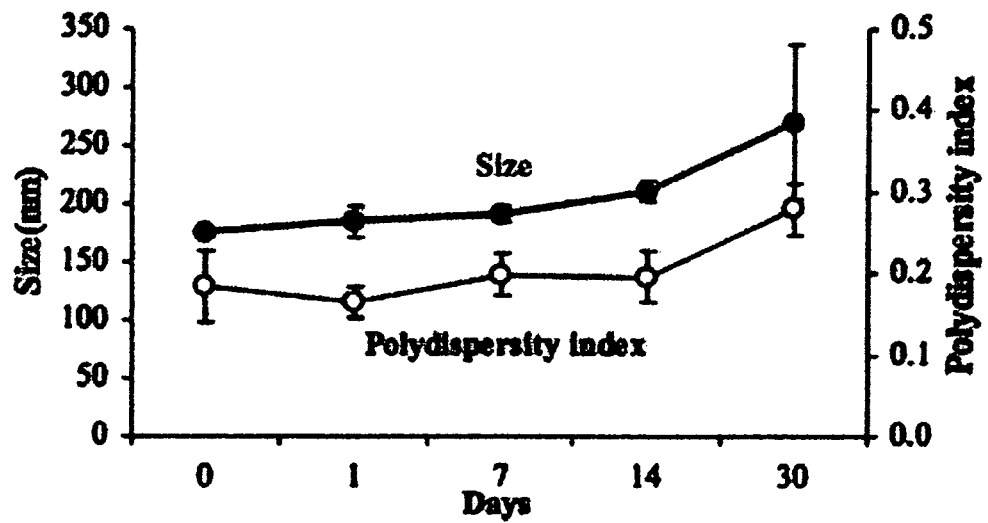
FIG. 2 is a graph showing size (in nanometers) and polydispersity index measurements of IgG-SPIO at different time points after conjugation when stored at 4° C.

The stability of IgG-SPIO was studied at 4° C. at selected time points for a period of one month by measures of size and polydispersity index (FIG. 2). Immediately after conjugation, IgG-SPIO were 175 nm in size and had a polydispersity index of approximately 0.2. No significant changes in hydrodynamic diameter and the size distribution were noticed during the first two weeks. However, 30 days after conjugation, IgG-SPIO increased up to 270 nm and the polydispersity index approximated 0.3, suggesting limited NP aggregation.

Example 2

Isolation and Cultivation of Monocytes, Monocyte-Derived Macrophages (MDM), and Bone Marrow-Derived Macrophages (BMM)

Human monocytes were obtained by leukopheresis from HIV-1 and hepatitis seronegative donors and were purified by counter-current centrifugal elutriation. Wright-stained cytospins were prepared and cell purity assayed by immuno-labeling with anti-CD68 (clone KP-1). To generate monocyte-derived macrophages (MDM), elutriated monocytes were cultivated for up to seven days at a concentration of 2×10$^6$ cells/ml at 37° C. in a humidified atmosphere in Dulbecco's modified Eagles medium (DMEM) supplemented with 10% heat-inactivated pooled human serum, 1% glutamine, 50 µg/ml gentamicin, 10 µg/ml ciprofloxacin and 1000 U/ml recombinant human macrophage colony stimulating factor (MCSF), a generous gift of Wyeth Inc., Cambridge, Mass. Male BALB/c mice (Charles River Laboratory, Inc., MA), 4-5 weeks of age were used as bone marrow-derived macrophage (BMM) donors. The femur was removed, the bone marrow expelled, cells dissociated into single cell suspensions and cultured for 10 days supplemented with 1000 units/ml of MCSF (Wyeth, Inc.). Cultured BMM proved to be 98% CD11b+ by flow cytometric analysis using a FACS Calibur flow cytometer (BD Biosciences).

Example 3

Uptake of Coated SPIO by Monocytes and Macrophages

Human monocytes or MDM were transferred in 8-well Lab-Tek II chamber slides ($0.5 \times 10^6$ cells/well). SPIO were added to a final iron concentration of 0.5 mg/ml and incubated for 1 hr at 37° C. After three washings, cells were fixed with 4% paraformaldehyde for 30 minutes at room temperature. For the Fc blocking studies, human IgG Fc fragment or anti-Fc receptor antibodies (clones 3G8, 3D3 and 10.1) (10 µg/ml) were added to MDM cultures, incubated at 37° C. for 20 minutes followed by the incubation of SPIO, IgG-SPIO, or F(ab')$_2$-SPIO to a final iron concentration of 0.5 mg/ml for 0.5, 1, 2 and 4 hours. Cells with media alone and with anti-TNP isotype control, 107.3 served as controls. For murine BMM, the procedure was identical to the human cells but mouse IgG Fc fragment and IgG FcgRIII/FcgRII were used as Fc blockers. After 2×PBS washes cells were observed by fluorescence microscopy.

The iron content was estimated by ferrozine (see below). Presence of iron was observed by Prussian blue staining with 5% potassium ferrocyanide and 5% hydrochloric acid. After three washings, cells were counterstained with nuclear fast red. A high accumulation of iron was observed with IgG-SPIO, whereas the uptake of native SPIO by human monocytes was limited. Viability of monocytes and MDM was estimated by a live/dead assay (Axxora, LLC, San Diego, Calif.). Iron labeled monocytes were incubated with a mixture of 0.5 µM of ethidium homodimer-1 with 1 µM of calcein AM at 37° C. under humidified atmosphere for 25 minutes. The cells were washed three times, fixed with 4% paraformaldehyde for 30 minutes at room temperature, and observed by fluorescent microscopy. Calcein-AM accumulation and cleavage by cytosolic esterase labels live cells green and ethidium homodimer-1 labels the nuclei of dead cells red. Human monocyte viability was consistently greater than 90%. Cell viability was confirmed by trypan blue exclusion wherein iron-labeled human monocytes were incubated with trypan blue for 15 minutes and washed three times. Most of the iron-labeled monocytes excluded trypan blue confirming that internalization of IgG-SPIO did not induce a toxic effect. Unlabeled cells and human monocytes that were killed using a 70% methanol solution served as controls.

Transmission electron microscopy (TEM) was used to study the location of SPIO in human monocytes. For TEM, human monocytes and MDM were cultivated on poly-d-lysine-coated Thermanox coverslips (Thermo Fisher Scientific, Rochester, N.Y.), incubated with SPIO during 1 hour at 37° C., and washed three times with phosphate buffered saline. They were fixed in 2% glutaraldehyde, 2% paraformaldehyde, 0.5% acrolein in 0.1M Sorensen's phosphate buffer pH 7.2, and were post-fixed in 1% osmium tetroxide in water for 30 minutes. After washing, human monocytes were dehydrated for 5 minutes at each step in a graded series of ethanol solutions and infiltrated with araldite embedding media by passing through a graded series of ethanol/araldite solutions. Coverslips were embedded culture side face down onto blank araldite discs, placed overnight in an oven at 65° C. for polymerization, and removed by dipping in liquid nitrogen. Monocyte and MDM colonies were cut out and mounted en face for ultra thin sectioning. Sections were placed on 200 mesh copper grids, and grids were stained with 1% uranyl acetate and Reynold's lead citrate. Cells were examined with a Philips LS410 TEM operated at 80 Kv. Accumulation of chromatin was observed in the nuclear periphery of human monocytes. IgG-SPIO was taken up in cells within endocytic vesicles with size reaching 0.7-1 µm. Distribution of IgG-SPIO was intracytoplasmic with preferential location of NP on small membrane ruffles. Both the number and the size of iron-loaded vesicles were increased in the IgG-SPIO formulations.

Iron content was estimated using a colorimetric ferrozine assay. For this assay, duplicate batches of human monocytes and MDM were cultivated in 24-well plates ($1 \times 10^6$ cells/well). SPIO were incubated at a final concentration of 0.5 mg/ml for 0.5, 1, 2, 4 and 8 hours, at 4° C. and 37° C. Iron-labeled cells were washed three times with PBS and lysed with 50 mM NaOH for 1 hr at room temperature on a shaker. Aliquots of cell lysates were mixed at equal volumes with 10 mM hydrochloric acid (HCl) in order to dissolve the SPIO. An iron releasing-reagent, a mixture of 1.4 M HCl and 4.5% (w/v) KMnO$_4$ in distilled water, was added to the lysates and the mixtures were incubated for 2 hour at 60° C. Ferrozine assay reagents were prepared in distilled water from 6 mM ferrozine, 2.5M ammonium acetate, 1M ascorbic acid and 6.5 mM neocuproine pre-dissolved in methanol. The samples were transferred to a 96-well plate and read at 540 nm. Iron standards were prepared under the same reaction conditions using a stock solution of iron at 0.2 mg/ml (Ricca Chemical Company, Arlington, Tex.). Iron concentration values were normalized to protein concentrations as determined by the micro BCA assay (Pierce Biotechnology).

Figure 3:
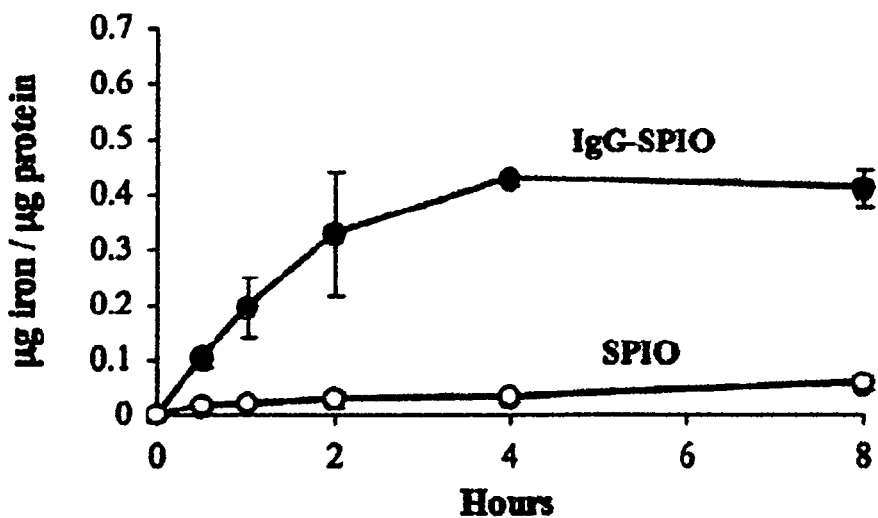
FIG. 3 is a graph showing uptake of SPIO and IgG-SPIO by monocytes after various periods of time, as assessed by a colorimetric ferrozine assay.

Covalent attachment of human IgG accelerated SPIO uptake as determined by calorimetric assays (FIG. 3). After 1 hour, the iron content of cells, ~0.2 µg iron/µg protein, reached half of the maximum value. In contrast to IgG-SPIO, the internalization of SPIO versus time was linear until 8 hours of incubation, passing from ~0.03 to 0.06 µg iron/µg protein between 4 and 8 hours. For the majority of times investigated, NP content was nearly an order of magnitude higher than that of cells treated with uncoated NP.

Figure 4:
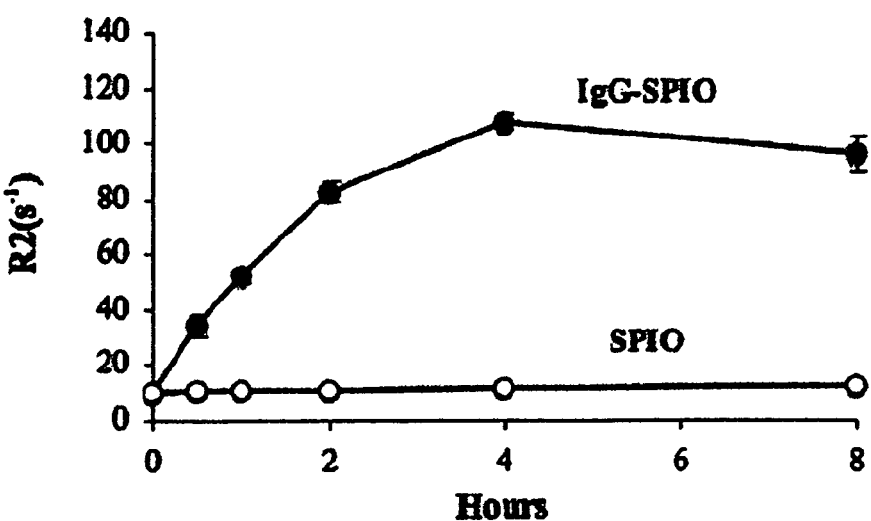
FIG. 4 is a graph showing uptake of SPIO and IgG-SPIO by monocytes after various periods of time, as assessed by measurement of relaxation (R2) by MRI.

$T_2$ relaxivity measurements of iron-labeled human monocytes were also performed by MRI analysis of triplicate samples for each time-point. MRI was used to detect the labeling of monocytes and ensure that the coupling procedure did not alter the NP magnetic properties. SPIO-labeled cell phantoms were prepared as 100 µl of $0.5 \times 10^6$ cells/ml suspended in 100 µl 2% agarose in 200 µl plastic tubes. In accordance with the results of the calorimetric ferrozine assay, the iron uptake was drastically improved when human monocytes were exposed to IgG-SPIO (FIG. 4). Maximal levels of SPIO were reached after a 4 hour-incubation. Despite the oxidation step, the relaxation properties of IgG-SPIO were preserved.

Example 4

Cellular Uptake of Particles

Figure 5:
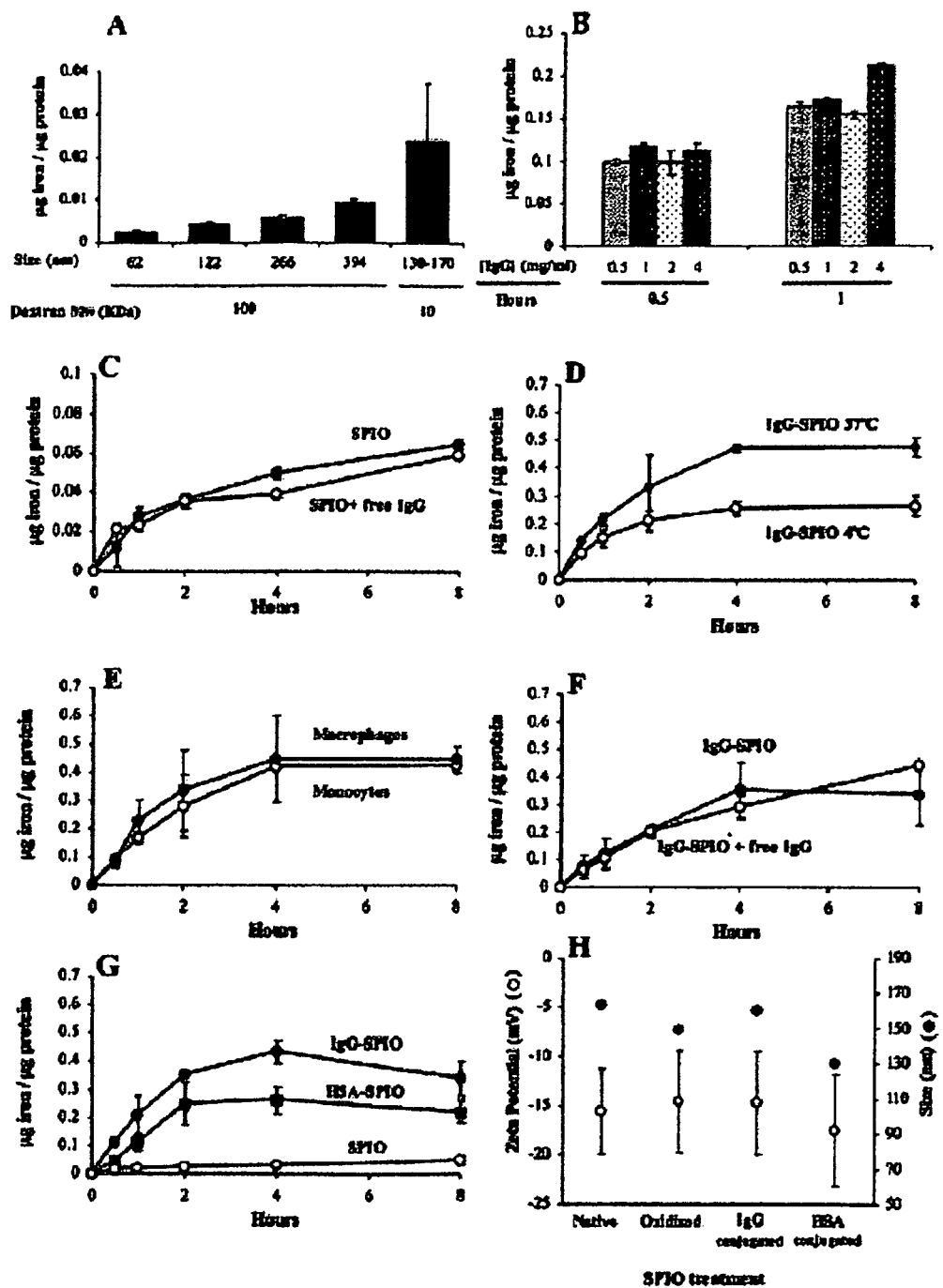
FIG. 5 provides graphs showing uptake of SPIO and IgG-SPIO by monocytes and macrophages under various conditions. (A) provides a graph of uptake by monocytes of SPIO particles of varying size (62 nm, 122 nm, 266 nm, and 394 nm) bound to 100 kDa dextran and of SPIO particles of 130-170 nm bound to 10 kDa dextran. (B) provides a graph of uptake by monocytes of IgG-SPIO particles prepared using solutions having varying concentrations of IgG. (C) provides a graph of uptake by monocytes of native SPIO incubated with free IgG. (D) provides a graph of uptake by monocytes of IgG-SPIO particles at 4° C. and at 37° C. (E) provides a graph of uptake by monocytes and monocyte-derived macrophages (MDM) of IgG-SPIO particles. (F) provides a graph of uptake by monocytes of IgG-SPIO particles co-incubated with an excess of free IgG. (G) provides a graph of uptake by monocytes of SPIO particles conjugated to human serum albumin (HSA). (H) provides a graph showing particle surface charge (zeta potential) and particle size for native, oxidized, IgG-conjugated, and HSA-conjugated SPIO particles.

To test the effect of size and dextran coating on cellular uptake, SPIO coated with 100 kDa dextran with sizes ranging from 62 to 394 nm were incubated with human monocytes for 1 hour at 37° C. (FIG. 5A). A greater iron uptake was detected for the largest NP with the same molecular weight of dextran. The SPIO coated with 10 kDa-dextran (Feridex®) were taken up in monocytes at a higher level than other NP coated with 100 kDa-dextran. After 1 hour-oxidation, SPIO was conjugated with different concentrations of IgG (0.5, 1, 2 and 4 mg/ml) and each conjugate IgG-SPIO complex was incubated with human monocytes for 0.5 and 1 hr at 37° C. Cellular uptake of IgG-SPIO prepared at different IgG concentrations was not drastically different after incubation with monocytes for 0.5 and 1 hour (FIG. 5B). These results suggested that either the cell surface was saturated by SPIO or that internalization is not dependent on ligand density. Non-covalent attachment of IgG did not induce an enhanced uptake for these specific experiments (FIG. 5C). Nonetheless, the steric barrier generated by the dextran surrounding the iron core of NP could have prevented adsorption of IgG. IgG-SPIO uptake was partially inhibited when incubation was performed at 4° C. (FIG. 5D). Next, IgG-SPIO uptake by monocytes and MDM were compared and found to be virtually equal for both cell types (FIG. 5E). The results support the idea that similar mechanisms for iron uptake were operative amongst both cell types. In order to study the mechanism of internalization, IgG-SPIO and free IgG, at a concentration of 1 mg/ml, were co-incubated with human monocytes (FIG. 5F). No significant differences were detected after the blocking of monocyte Fc receptors with free IgG. These results suggested an Fc receptor-independent mechanism for IgG-SPIO cell entry. To test that possibility, human serum albumin (HSA) was covalently attached to SPIO using the identical oxidation/reduction procedure as IgG conjugation. Similar to IgG, HSA significantly enhanced the uptake of SPIO (FIG. 5G). In order to confirm the notion that particle uptake was independent of the Fc receptor we performed blocking studies. Regression analysis of intracellular iron of IgG-SPIO and F(ab')2-SPIO uptake by MDM over 4 hours of co-culture showed no differences in uptake kinetics (P=0.271), indicating that the presence of the IgG Fc portion provided no significant advantage for IgG-SPIO uptake kinetics. Similarly, no differences in IgG-SPIO uptake kinetics were discernable by treatment of MDM with human Fc fragments, anti-Fc receptor-γ antibodies (CD16/CD32/CD64), or isotype control antibody compared to untreated MDM (P=0.624). Additionally, results in human MDM were validated in mouse BMM wherein no differences were observed in uptake kinetics of mouse IgG-SPIO by BMM treated with mouse Fc fragments, rat anti-mouse Fc receptor-γ (CD16/CD32), or rat isotype control antibody compared to untreated BMM (P=0.988). These results confirmed the hypothesis that the internalization of IgG-SPIO was not Fc-receptor mediated. Although internalization of HSA-SPIO was similar to IgG-SPIO, the iron content in human monocytes was higher in monocytes incubated with IgG-SPIO than HSA-SPIO. This could be due to the fact that HSA modified the conjugated SPIO itself. To test the latter possibility, physical-chemical properties of SPIO including zeta potential and size measurements of the nanoparticles were performed in HEPES buffer at pH 7.4. HSA modifications of the SPIO did not affect its size (FIG. 5H). In addition, the zeta potential of NP did not significantly change after ligand attachment; thus, SPIO remained negatively charged.

Example 5

Imaging of SPIO and IgG-SPIO Tissue Distribution in Mice by MRI

Male BALB/c mice (Charles River Laboratory, Inc., Wilmington, Mass.), 5-8 weeks old were used for all experiments. Animals were housed in sterile microisolator cages and maintained in accordance with ethical guidelines for the care of laboratory animals of University of Nebraska Medical Center and the National Institutes of Health. Mice were injected with SPIO or IgG-SPIO at either 12.5 μg/0.2 ml/mouse or 62.5 μg/0.2 ml/mouse intravenously via the tail vein. The recommended dose for a human adult or adolescent is 560 μg/kg. Two groups of mice with 3-5 animals per group were used for in vivo analyses. SPIO and IgG-SPIO treated groups were imaged before injection, continuously for 4 hours after injection, and again at 24 hours. Mice were injected within 24 hours following preparation of conjugated SPIO.

SPIO particle accumulation in tissue causes an increase in the magnetic spin-spin relaxivity ($R_2$) of tissue water, which is field-dependent. Measures of spin-spin relaxivity using two 7T MRI systems (Bruker 21 cm Biospec/16 cm Pharmascan systems operating Paravision 4.0) demonstrated in SPIO-labeled cell phantoms that relaxivity is related directly to cell density. Measures of relaxivity can track cell uptake and has been used to track the migration of cells to liver, kidney and spleen after injection. High-resolution, multislice multi-echo CPMG phase cycled $T_2$ mapping MRI scans of mouse body were acquired using a 25-mm birdcage volume coil covering a region from the neck to the hips with acquisition parameters of echo time (TE)=10, 20, 30, 40, 50, 60, 70, 80 ms, repetition time (TR)=4650 ms, number of averages (NA)=4, field of view=40×40 mm with a resolution of 256×128 (voxel size=156×312 μm), reconstructed to 256×256, 50 interleaved contiguous 1 mm thick slices, total acquisition time=39 minutes. Signal intensity was normalized to an external standard to account for signal drift over time. SPIO accumulation was determined by changes in $R_2$ ($1/T_2$) within selected regions of interest. After the injection of SPIO or IgG-SPIO, $T_2$ maps were acquired every 40 minutes for 4 hours, and at 24 hours. Intensities of the regions of interest in spleen, liver and kidney from the even numbered echoes (accurately refocused in CPMG phase cycled echo trains) were fit to an exponential decay with a minimum to match the noise level measured in the images. Data quality was monitored by the $T_2$ determination of external standards in each set of images.

Figure 6:
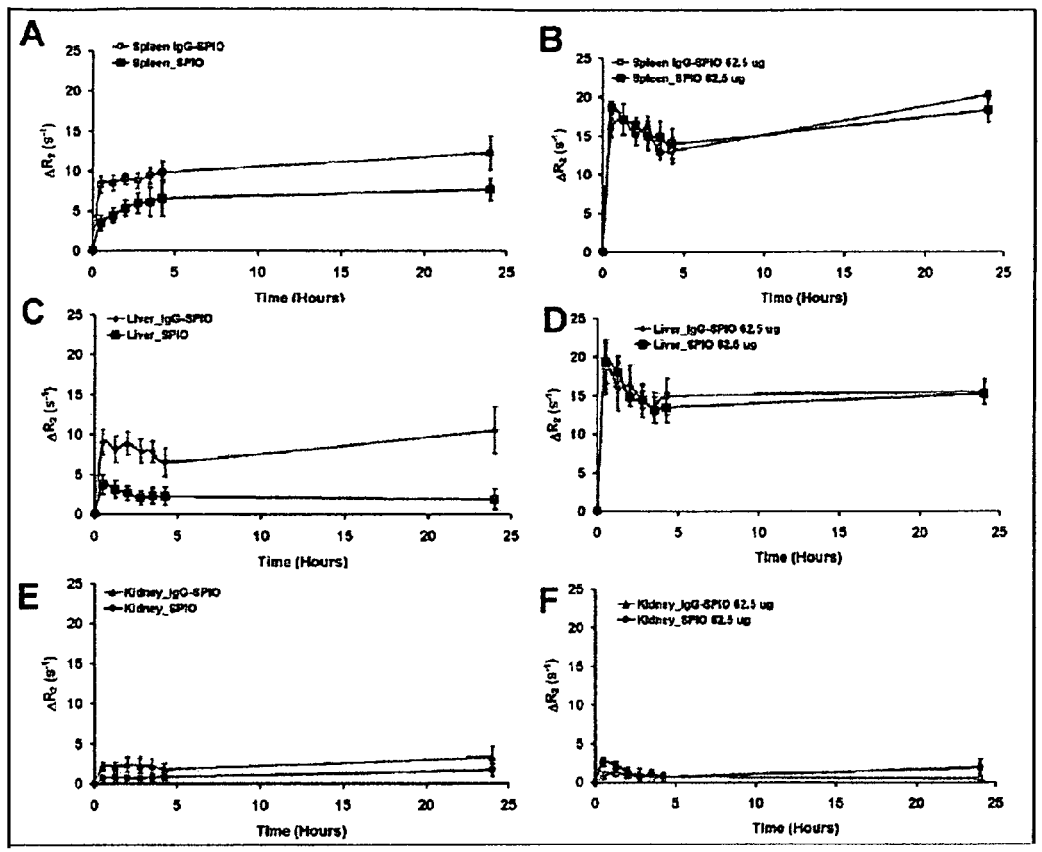
FIG. 6 provides graphs showing quantification of in vivo SPIO and IgG-SPIO particles using CPMG phase cycled $T_2$ mapping MRI. (A) is a graph showing the change in relaxivity ($R_2=1/T_2$) in the spleen after injection of 12.5 μg of SPIO or IgG-SPIO into the tail vein of mice (n=6). (B) is a graph showing the change in relaxivity ($R_2=1/T_2$) in the spleen after injection of 62.5 μg of SPIO or IgG-SPIO into the tail vein of mice (n=5). (C) is a graph showing the change in relaxivity ($R_2=1/T_2$) in the liver after injection of 12.5 μg of SPIO or IgG-SPIO into the tail vein of mice (n=6). (D) is a graph showing the change in relaxivity ($R_2=1/T_2$) in the liver after injection of 62.5 μg of SPIO or IgG-SPIO into the tail vein of mice (n=6). (E) is a graph showing the change in relaxivity ($R_2=1/T_2$) in the kidney after injection of 12.5 μg of SPIO or IgG-SPIO into the tail vein of mice (n=6). (F) is a graph showing the change in relaxivity ($R_2=1/T_2$) in the kidney after injection of 62.5 μg of SPIO or IgG-SPIO into the tail vein of mice (n=5).

Change in relaxivity ($R_2=1/T_2$) were measured in the spleen (FIGS. 6A and 7B), liver (FIGS. 6C and 6D), and kidney (FIGS. 6E and 6F) after injection of SPIO or IgG-SPIO into the tail vein of the mouse. Injections of 12.5 μg (FIGS. 6A, 6C, and 6E) (n=6) and 62.5 μg (FIGS. 6B, 6D, and 6F) (n=5) show higher uptake in circulating monocytes with IgG coating at the lower concentration by 0.5 h post-injection and times thereafter (p<0.05, two way repeated measures ANOVA for effect of time and SPIO type for spleen and liver). At the higher 62.5 μg dosage, no differences in uptake of SPIO compared to IgG-SPIO were observed at any time point.

Example 6

Histological Evaluations

Spleens and livers were collected at 4 and 24 hours after SPIO or IgG-SPIO administration. Immediately after MRI, tissues were fixed by perfusion with 4% paraformaldehyde, post fixed for 24 hours, embedded in paraffin and cut into 5 μm thick sections for histological analysis. For Prussian blue staining, slide mounted sections were deparaffinized, rehydrated, and reacted for 30 minutes in 2% potassium ferrocyanide and 3.7% hydrochloric acid to visualize ferric iron particles by Prussian blue. Stained sections were washed and counter stained with nuclear fast red to provide histological cellular distributions. Images were obtained by Optronics digital camera (Buffalo Grove, Ill.) with MagnaFire 2.0 software (Goleta, Calif.) and processed by Adobe® Photoshop 7.0 software. Signal loss from the accumulation of SPIO was observed in the 0.5 hour and 24 hour images.

Uptake of SPIO was seen in circulating blood monocytes and tissue macrophages by analysis of tissue specimens from spleen and liver of animals that were injected with Alexa Fluor® 488 hydroxylamine IgG-SPIO nanoformulations following the MRI tests.

Example 7

Preparation of Paclitaxel Particles with IgG Coating

Crystalline paclitaxel particles were prepared by precipitating the drug from a water-miscible organic solvent into an aqueous solution containing surfactants, followed by a homogenization step using a piston-gap homogenizer. The surfactants, which were used to prevent particle aggregation, were used in various combinations to generate nanosuspension formulations PTX-1, PTX-2 and PTX-3. All of the paclitaxel nanosuspensions were buffered to pH 7.8-7.9 using 10 mM phosphate buffer. The mean size of the paclitaxel particles was in the range of 150-300 nm, as measured by laser light scattering (Horiba LA-920, relative refractive index=16A001I). The zeta potential of the paclitaxel particles was measured using 10 mM HEPES buffer pH 7.4 as diluent (Malvern Nano ZS). The zeta potential values of the paclitaxel suspensions before IgG coating are given in Table 1.

TABLE 1

| Formulation | Components | Zeta Potential of Paclitaxel (PTX) Nanosuspensions, pH 7.4 (mV) |
|---|---|---|
| PTX-1 | Poloxamer 188 deoxycholate | −30.5 |
| PTX-2 | Poloxamer 188 1,2-dimyristoyl-sn-glycero-3-[phospho-rac-(1-glycerol)] (DMPG) | −40.3 |
| PTX-3 | Poloxamer 188 1,2-distearoyl-sn-glycero-3-phosphoethanolamine-methoxypolyethylene glycol (DSPE-MPEG2000) | −22.7 |

Particles of paclitaxel having a coating of human IgG were prepared by incubating paclitaxel nanosuspensions with IgG solutions at various weight ratios of IgG:paclitaxel at room temperature. IgG solutions were prepared by diluting a commercially available product (GAMMAGARD LIQUID 10%, Baxter Healthcare) with 0.25M glycine buffer pH 5 to final concentrations of 50, 25, 10, 5, and 2.5 mg/mL IgG. To confirm that the changes in zeta potential observed after incubation with IgG were due to IgG adsorption and not due to the high ionic strength of the IgG buffer solution, incubations were also performed in the glycine buffer alone (no IgG).

IgG adsorption was probed by measuring the zeta potential of the IgG-nanosuspension mixtures. The measurements were performed at pH 5 and at pH 7.4 using 10 mM glycine and 10 mM HEPES buffers, respectively, as diluents. The Smoluchowsky model was used to calculate zeta potentials from the measured electrophoretic mobilities.

Figure 7:
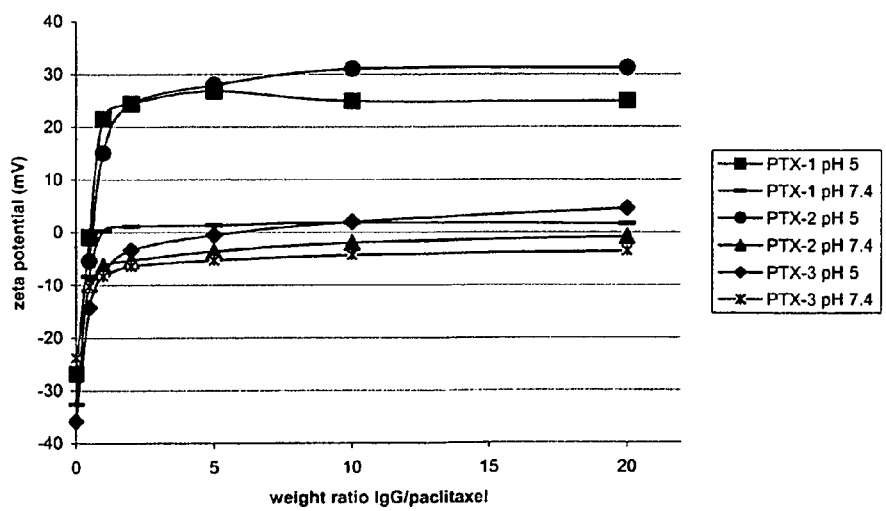
FIG. 7 is a graph showing zeta potential for IgG-coated paclitaxel particles at various ratios of IgG to paclitaxel.

FIG. 7 shows the results of the adsorption experiments for the paclitaxel formulations. The data indicate that for all three formulations, the zeta potential is markedly affected by the presence of IgG (lines are guides to the eye only). At pH 5, IgG has a net positive charge (isoelectric point=6.9-7.3) whereas the drug particles are negatively charged. All three suspensions show a zeta potential near zero when measured at pH 7.4, slightly above the isoelectric point of IgG. At this pH, the zeta potential is still significantly different from the uncoated values, indicating that IgG is still adsorbed on the surface.

The effect of IgG adsorption on the physical stability of the suspension was determined through microscopic observation at 400× magnification. For some nanosuspension formulations, incubation with IgG resulted in aggregation of the drug particles. For these formulations, it is hypothesized that the IgG adsorption results in levels of surface charge on the particles that are insufficient to provide electrostatic stabilization of the suspension.

Example 8

Preparation of Ritonavir Particles with IgG Coating

Crystalline ritonavir particles were prepared by homogenization of the drug crystals in the presence of an aqueous solution containing DSPE-MPEG(2000) buffered to pH 7.7 using 10 mM phosphate buffer. The mean particle size was approximately 0.5 micron, as measured by laser light scattering (Horiba LA-920, relative refractive index=120A010I). The zeta potential of this suspension was −49.8 mV using 1 mM HEPES buffer pH 7.4 as diluent (Malvern Nano ZS, Smoluchowsky model).

Particles of ritonavir having a coating of human IgG were prepared by incubating ritonavir suspensions with IgG solutions. The weight ratio of IgG:ritonavir was varied by either diluting the IgG solution with glycine buffer as described in Example 7, or by varying the volume ratio of ritonavir suspension to neat (100 mg/mL) IgG solution.

Figure 8:
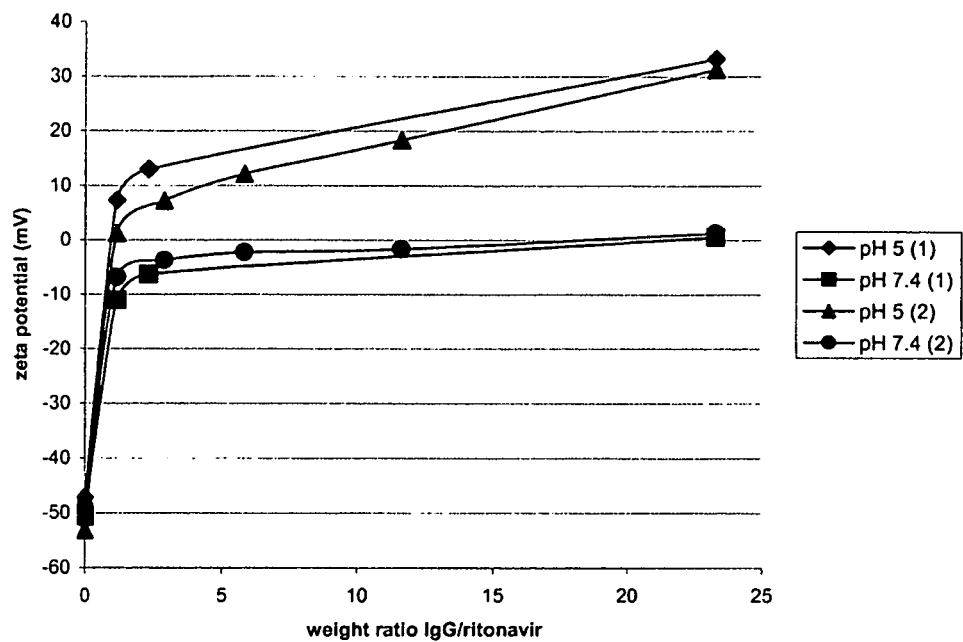
FIG. 8 is a graph showing zeta potential for IgG-coated ritonavir particles at various ratios of IgG to ritonavir.

Zeta potential measurements were performed at pH 5 and at pH 7.4 using 1 mM glycine and 1 mM HEPES buffers, respectively, as diluents. The pH of the diluted samples in pH 7.4 buffer was measured to confirm that addition of the suspension/IgG mixture did not appreciably change the pH of the buffer. The zeta potential data resulting from the two approaches to IgG coating were found to be in good agreement (FIG. 8). Aggregation of the IgG-coated ritonavir particles was assessed according to the procedure described in Example 7. No aggregation was observed by microscopic observation at any weight ratio of IgG:ritonavir.

Example 9

Preparation of Indinavir Particles with IgG Coating

Crystalline indinavir particles were prepared by homogenization of the drug crystals in the presence of an aqueous solution containing Poloxamer 188 and 1,2-distearoyl-sn-glycero-3-phosphoethanolamine-methoxypolyethylene glycol (DSPE-MPEG2000) buffered to pH 7.8 using 10 mM HEPES buffer. The mean particle size was approximately 0.9 micron, as measured by laser light scattering (Horiba LA-920, relative refractive index=108A000I).

Particles of indinavir having a coating of human IgG were prepared by incubating indinavir suspension with neat GAMMAGARD LIQUID 10% (Baxter Healthcare). The procedure involved combining 0.5 mL of 2.22% (w/v) indinavir suspension (equivalent to 11.1 mg of drug) with 0.33 mL of the 10% IgG solution to achieve a 3:1 weight ratio of IgG:indinavir.

In parallel, particles of indinavir having a coating of murine IgG were prepared by incubating indinavir suspension with murine IgG (Sigma). The lyophilized murine IgG (10 mg) was reconstituted with 1 mL of 0.9% sodium chloride solution. 0.15 mL of indinavir suspension was then added to the vial to achieve a 3:1 weight ratio of IgG:indinavir. Microscopic examination at 400× magnification indicated that the particles did not aggregate in the presence of either the human or the murine IgG.

Zeta potential was measured using 1 mM HEPES buffer pH 7.4 as diluent (Malvern Nano ZS, Smoluchowsky model). The results are given in Table 2. The substantial decrease in negative surface charge for the suspensions incubated with the IgG solutions is indicative of IgG adsorption at the particle surface.

TABLE 2

| Formulation | Zeta Potential of Indinavir (IDV) Suspension, pH 7.4 (mV) |
| --- | --- |
| IDV suspension | −45.4 |
| IDV suspension + human IgG | −1.78 |
| IDV suspension + murine IgG | −6.96 |

Example 10

Preparation of Celecoxib Particles with IgG Coating

Crystalline celecoxib particles were prepared by either precipitation from organic solvent followed by homogenization (CXB-2) or by direct homogenization of the drug crystals (CXB-1, CXB-3). The particles were prepared using aqueous solutions containing surfactants buffered to pH 7.5-7.8 using 10 mM phosphate buffer. Particles of celecoxib having a coating of human IgG were prepared using a 10% solution of IgG according to the procedure described in Example 7.

The formulation components, volume-weighted mean particle size measurements, and zeta potential measurements for the celecoxib suspensions are provided in Table 3. Particle size was measured by laser light scattering (Horiba LA-920, relative refractive index=19A001I). Zeta potential was measured using either 10 mM (CXB-1, CXB-2) or 1 mM (CXB-3) HEPES buffer pH 7.4 as diluent (Malvern Nano ZS, Smoluchowsky model). The decrease in negative surface charge for the suspensions incubated with the IgG solution is indicative of IgG adsorption at the particle surface.

Example 11

Uptake of IgG-Coated Paclitaxel Particles

Fluorescently labeled paclitaxel particles were prepared using 0.5 g paclitaxel and 400 μg Oregon Green labeled paclitaxel (available from Invitrogen). The fluorescently labeled paclitaxel particles (particle size approximately 160 nm to 170 nm) were coated by adding 0.2 mL of a 10% intravenous immunoglobulin (IVIG) solution to 0.1 mL of a paclitaxel suspension. Fluorescently labeled paclitaxel particles also were coated with protamine by adding 0.8 mL of a 25 mg/mL protamine solution to 0.1 mL of a paclitaxel suspension.

Figure 9:
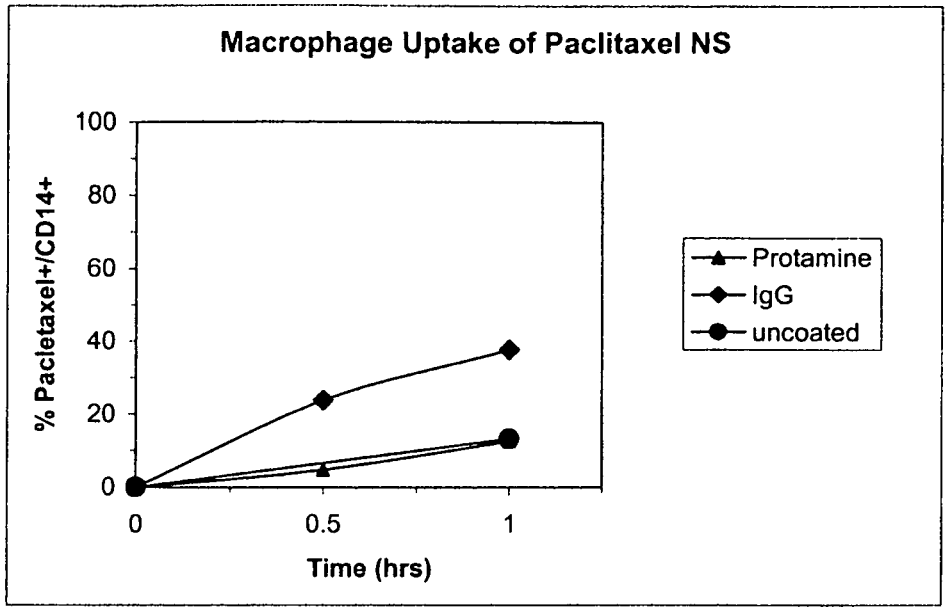
FIG. 9 is a graph showing uptake of uncoated paclitaxel particles labeled with Oregon Green (uncoated), IgG-coated paclitaxel particles labeled with Oregon Green (IgG) and protamine-coated paclitaxel particles labeled with Oregon Green (Protamine).
Figure 10:
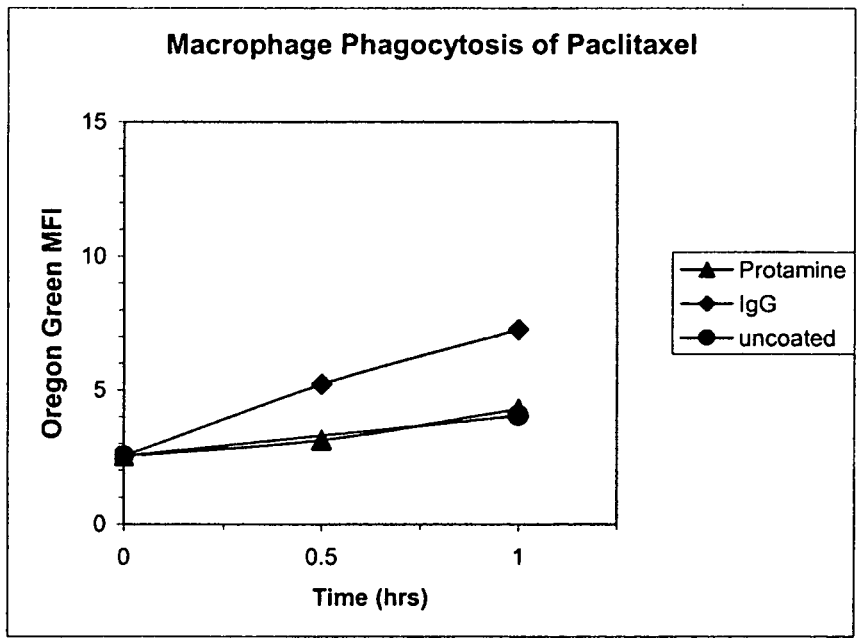
FIG. 10 is a graph showing uptake of uncoated paclitaxel particles (uncoated), IgG-coated paclitaxel particles labeled with Oregon Green (IgG) and protamine-coated paclitaxel particles labeled with Oregon Green (Protamine).

The uptake kinetics of the paclitaxel nanosuspensions are shown in FIG. 9 and FIG. 10 (results are shown as both percentages of paclitaxel positive cells after nanosuspension uptake and MFI of cell associated/internalized particles). The IgG coating improved the uptake of particles compared to untreated particles.

Figure 11:
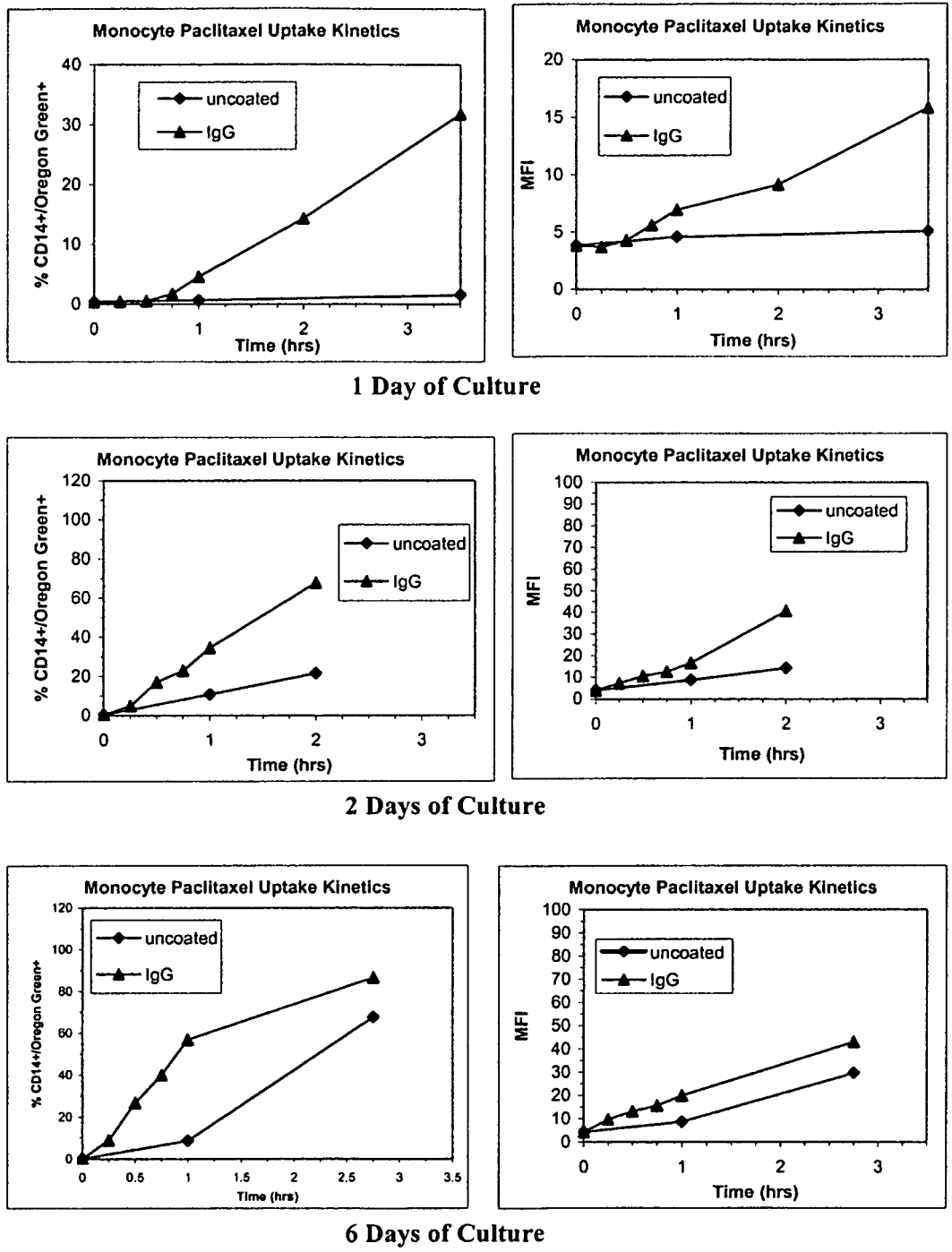
FIG. 11 provides graphs showing uptake of uncoated paclitaxel particles labeled with Oregon Green (uncoated) and IgG-coated paclitaxel particles labeled with Oregon Green (IgG).

FIG. 11 shows uptake by monocytes of IgG-coated paclitaxel nanosuspensions after 1, 2, or 6 days of culture. The results indicate that the longer the cells are cultured, the more responsive they are to IgG.

While specific embodiments have been illustrated and described, numerous modifications come to mind without departing from the spirit of the invention and the scope of protection is only limited by the scope of the accompanying claims.

What is claimed is:

1. A pharmaceutical composition comprising a suspension containing a surface-modified particle, said surface-modified particle comprising a particle core and a coating associated with the particle core, said coating being adsorbed to a surface of the particle core, wherein the particle core comprises a therapeutic agent, the coating comprises an opsonin, the particle core is negatively charged, the particle core has hydrophobic regions on the particle core surface, the surface-modified particle has an average size from about 1 nm to about 2,000 nm, the pH of the suspension is below the isoelectric point of the opsonin, and the opsonin is selected from the group consisting of an antibody having an isotype of IgG, complement protein C3b, and complement protein C5.

2. The pharmaceutical composition of claim 1, said coating being adsorbed to a surface of the particle core and further

TABLE 3

| Formulation | Components | Zeta Potential of Uncoated Celecoxib Nanosuspensions, pH 7.4 (mV) | Zeta Potential of IgG-coated Celecoxib Nanosuspensions, pH 7.4 (mV) | Mean Particle Size (nm) |
| --- | --- | --- | --- | --- |
| CXB-1 | Lipoid E80<br>1,2-dimyristoyl-sn-glycero-3-[phospho-rac-(1-glycerol)] (DMPG) | −69.9 | −0.663 | 1220 |
| CXB-2 | Poloxamer 188<br>1,2-distearoyl-sn-glycero-3-phosphoethanolamine-methoxypolyethylene glycol (DSPE-MPEG2000) | −21.7 | −4.87 | 315 |
| CXB-3 | Poloxamer 188<br>Polysorbate 80 | −20.6 | −8.18 | 988 | comprising a polysaccharide, and said opsonin being covalently attached to the polysaccharide.

3. The pharmaceutical composition of claim 2, wherein the polysaccharide is dextran.

4. The pharmaceutical composition of claim 2, wherein the polysaccharide has a molecular weight between about 5,000 daltons and about 250,000 daltons.

5. The pharmaceutical composition of claim 1, wherein the coating further comprises a surfactant.

6. The pharmaceutical composition of claim 5, wherein the surfactant is selected from the group consisting of anionic surfactants, cationic surfactants, zwitterionic surfactants, nonionic surfactants, surface active biological modifiers, and combinations thereof.

7. The pharmaceutical composition of claim 5, wherein the surfactant comprises at least one of a poloxamer and a phospholipid.

8. The pharmaceutical composition of claim 1, wherein the therapeutic agent is selected from the group consisting of analgesics, anesthetics, analeptics, adrenergic agents, adrenergic blocking agents, adrenolytics, adrenocorticoids, adrenomimetics, anticholinergic agents, anticholinesterases, anticonvulsants, alkylating agents, alkaloids, allosteric inhibitors, anabolic steroids, anorexiants, antacids, antidiarrheals, antidotes, antifolics, antipyretics, antirheumatic agents, psychotherapeutic agents, neural blocking agents, anti-inflammatory agents, antihelmintics, antibiotics, anticoagulants, antidepressants, antiepileptics, antifungals, anti-infective agents, anti-parasitic agents, antihistamines, antimuscarinic agents, antimycobacterial agents, antineoplastic agents, antiprotozoal agents, antiviral agents, anxiolytic sedatives, beta-adrenoceptor blocking agents, corticosteroids, cough suppressants, dopaminergics, hemostatics, hematological agents, hypnotics, immunological agents, muscarinics, parasympathomimetics, prostaglandins, radiopharmaceuticals, sedatives, stimulants, sympathomimetics, vitamins, xanthines, growth factors, hormones, antiprion agents, and combinations thereof.

9. The pharmaceutical composition of claim 1, wherein the therapeutic agent is an antineoplastic agent selected from the group consisting of paclitaxel, paclitaxel derivative compounds, alkaloids, antimetabolites, enzyme inhibitors, alkylating agents, and combinations thereof.

10. The pharmaceutical composition of claim 1, wherein the therapeutic agent is a protease inhibitor.

11. The pharmaceutical composition of claim 10, wherein the protease inhibitor is selected from the group consisting of indinavir, ritonavir, saquinavir, nelfinavir, and combinations thereof.

12. The pharmaceutical composition of claim 1, wherein the therapeutic agent is a nucleoside reverse transcriptase inhibitor.

13. The pharmaceutical composition of claim 12, wherein the nucleoside reverse transcriptase inhibitor is selected from the group consisting of zidovudine, didanosine, stavudine, zalcitabine, lamivudine and combinations thereof.

14. The pharmaceutical composition of claim 1, wherein the therapeutic agent is a non-nucleoside reverse transcriptase inhibitor.

15. The pharmaceutical composition of claim 14, wherein the non-nucleoside reverse transcriptase inhibitor is selected from the group consisting of efavirenz, nevirapine, delaviradine, and combinations thereof.

16. The pharmaceutical composition of claim 1, wherein the therapeutic agent is an anti-inflammatory agent.

17. The pharmaceutical composition of claim 16, wherein the anti-inflammatory agent is selected from the group consisting of non-steroidal anti-inflammatory drugs, non-selective cycloxygenase (COX) inhibitors, COX-1 inhibitors, COX-2 inhibitors, lipoxygenase inhibitors, corticosteroids, anti-oxidants, tumor necrosis factor (TNF) inhibitors, and combinations thereof.

18. The pharmaceutical composition of claim 1, wherein the therapeutic agent is selected from the group consisting of celecoxib, rofecoxib, valdecoxib, parecoxib, lumiracoxib, etoricoxib, and combinations thereof.

19. The pharmaceutical composition of claim 1, wherein the therapeutic agent is a biologic.

20. The pharmaceutical composition of claim 19, wherein the biologic is selected from the group consisting of proteins, polypeptides, carbohydrates, polynucleotides, nucleic acids, and complexes, conjugates, and combinations thereof.

21. The pharmaceutical composition of claim 1, wherein the therapeutic agent is a pharmaceutical compound.

22. The pharmaceutical composition of claim 1, wherein the opsonin is human IgG.

23. The pharmaceutical composition of claim 1, wherein the opsonin is intravenous immunoglobulin (IVIG).

* * * * *